(12) United States Patent
Shih et al.

(10) Patent No.: US 9,274,087 B2
(45) Date of Patent: Mar. 1, 2016

(54) PIEZOELECTRIC MICROCANTILEVER SENSORS FOR BIOSENSING

(71) Applicants: Wan Y. Shih, Bryn Mawr, PA (US); Wei-Heng Shih, Bryn Mawr, PA (US); Zuyan Shen, Philadelphia, PA (US); John-Paul McGovern, Philadelphia, PA (US); Qing Zhu, Philadelphia, PA (US); Joseph Capobianco, Sicklerville, NJ (US)

(72) Inventors: Wan Y. Shih, Bryn Mawr, PA (US); Wei-Heng Shih, Bryn Mawr, PA (US); Zuyan Shen, Philadelphia, PA (US); John-Paul McGovern, Philadelphia, PA (US); Qing Zhu, Philadelphia, PA (US); Joseph Capobianco, Sicklerville, NJ (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/551,710

(22) Filed: Nov. 24, 2014

(65) Prior Publication Data
US 2015/0105294 A1    Apr. 16, 2015

Related U.S. Application Data

(62) Division of application No. 12/514,941, filed as application No. PCT/US2007/085771 on Nov. 28, 2007, now Pat. No. 8,927,259.

(60) Provisional application No. 60/867,538, filed on Nov. 28, 2006.

(51) Int. Cl.
C12M 1/34    (2006.01)
C12M 3/00    (2006.01)
(Continued)

(52) U.S. Cl.
CPC ............ *G01N 29/022* (2013.01); *G01N 29/036* (2013.01); *G01N 29/245* (2013.01); *G01N 33/54306* (2013.01); *G01N 33/57415* (2013.01); *B82Y 5/00* (2013.01); *B82Y 35/00* (2013.01); *G01N 2291/0255* (2013.01); *G01N 2291/0256* (2013.01); *G01N 2291/0257* (2013.01); *G01N 2291/0427* (2013.01)

(58) Field of Classification Search
None
See application file for complete search history.

(56) References Cited

U.S. PATENT DOCUMENTS

| 3,205,464 A | 9/1965 | Schwartz |
| 4,093,883 A | 6/1978 | Yamamoto |

(Continued)

FOREIGN PATENT DOCUMENTS

| EP | 0631319 A1 | 12/1994 |
| EP | 1536227 A2 | 6/2005 |

(Continued)

OTHER PUBLICATIONS

Lee, C. et al., "Sol-gel derived PZT force sensor for scanning force microscopy", Mater. Chem. Phys., 44: 25-29 (1996).

(Continued)

*Primary Examiner* — Robert T Crow
(74) *Attorney, Agent, or Firm* — Mendelsohn Dunleavy, PC

(57) ABSTRACT

A piezoelectric microcantilever for sensing compounds or molecules. The piezoelectric microcantilever, may include at least one electrode, an insulation layer, a receptor, an immobilization layer, a non-piezoelectric layer and a piezoelectric layer The sensor is capable of self actuation and detection. The piezoelectric layer may be constructed from a highly piezoelectric thin lead magnesium niobate-lead titanate film, a highly piezoelectric thin zirconate titanate film, a highly piezoelectric lead-free film. Methods of using the sensors and flow cells and arrays including the sensors are also described.

20 Claims, 26 Drawing Sheets

(51) Int. Cl.
*C12M 1/00* (2006.01)
*G01F 15/00* (2006.01)
*G01N 29/02* (2006.01)
*G01N 29/036* (2006.01)
*G01N 29/24* (2006.01)
*G01N 33/543* (2006.01)
*G01N 33/574* (2006.01)
*B82Y 5/00* (2011.01)
*B82Y 35/00* (2011.01)

(56) References Cited

U.S. PATENT DOCUMENTS

| | | | |
|---|---|---|---|
| 4,302,694 | A | 11/1981 | Fujishima et al. |
| 4,349,762 | A | 9/1982 | Kitamura et al. |
| 4,363,993 | A | 12/1982 | Nishigaki et al. |
| 4,528,502 | A | 7/1985 | Rocha |
| 4,649,312 | A | 3/1987 | Robin et al. |
| 4,802,371 | A | 2/1989 | Calderara et al. |
| 5,054,323 | A | 10/1991 | Hubbard et al. |
| 5,313,535 | A | 5/1994 | Williams |
| 5,334,835 | A | 8/1994 | Nakayama et al. |
| 5,338,999 | A | 8/1994 | Ramakrishnan et al. |
| 5,382,864 | A | 1/1995 | Moikawa et al. |
| 5,445,008 | A | 8/1995 | Wachter et al. |
| 5,475,318 | A | 12/1995 | Marcus et al. |
| 5,503,010 | A | 4/1996 | Yamanaka |
| 5,553,486 | A | 9/1996 | Bonin |
| 5,626,728 | A | 5/1997 | Ramakrishnan et al. |
| 5,689,063 | A | 11/1997 | Fujiu et al. |
| 5,719,324 | A | 2/1998 | Thundat et al. |
| 5,780,727 | A | 7/1998 | Gimzewski et al. |
| 5,807,758 | A | 9/1998 | Lee et al. |
| 5,866,807 | A | 2/1999 | Elings et al. |
| 5,874,126 | A | 2/1999 | Kahn et al. |
| 5,948,993 | A | 9/1999 | Ting et al. |
| 5,966,787 | A | 10/1999 | Nakayama et al. |
| 5,996,412 | A | 12/1999 | Hansen |
| 6,075,585 | A | 6/2000 | Minne et al. |
| 6,278,379 | B1 | 8/2001 | Allen et al. |
| 6,280,396 | B1 | 8/2001 | Clark |
| 6,289,717 | B1 | 9/2001 | Thundat et al. |
| 6,336,366 | B1 | 1/2002 | Thundat et al. |
| 6,422,069 | B1 | 7/2002 | Shimizu et al. |
| 6,458,327 | B1 | 10/2002 | Vossmeyer et al. |
| 6,465,368 | B2 | 10/2002 | Inoue et al. |
| 6,589,727 | B1 | 7/2003 | Klenerman et al. |
| 6,621,080 | B2 | 9/2003 | Yamamoto |
| 6,734,425 | B2 | 5/2004 | Hantschel et al. |
| 6,781,285 | B1 | 8/2004 | Lazarus et al. |
| 6,903,491 | B2 | 6/2005 | Irie et al. |
| 6,992,421 | B2 | 1/2006 | Ikeda et al. |
| 7,055,378 | B2 | 6/2006 | Su et al. |
| 7,083,270 | B2 | 8/2006 | Torii et al. |
| 7,084,554 | B2 | 8/2006 | Xu et al. |
| 7,104,134 | B2 | 9/2006 | Amano et al. |
| 7,195,909 | B2 | 3/2007 | Klenerman et al. |
| 7,263,874 | B2 | 9/2007 | Fitch et al. |
| 7,335,345 | B2 | 2/2008 | Shih et al. |
| 7,458,265 | B2 | 12/2008 | Shih et al. |
| 7,497,133 | B2 | 3/2009 | Shih et al. |
| 7,597,870 | B2 | 10/2009 | Shih et al. |
| 7,744,773 | B2 | 6/2010 | Shih et al. |
| 7,942,056 | B2 | 5/2011 | Mutharasan et al. |
| 7,992,431 | B2 | 8/2011 | Shih et al. |
| 8,927,259 | B2 * | 1/2015 | Shih .............. G01N 29/022 116/275 |
| 2002/0094528 | A1 | 7/2002 | Salafsky |
| 2002/0117659 | A1 | 8/2002 | Lieber et al. |
| 2002/0155303 | A1 | 10/2002 | Wielstra et al. |
| 2003/0032293 | A1 | 2/2003 | Kim et al. |
| 2003/0068655 | A1 | 4/2003 | Bottomley et al. |
| 2003/0194697 | A1 | 10/2003 | Klenerman et al. |
| 2003/0224551 | A1 | 12/2003 | Kim et al. |
| 2003/0235681 | A1 | 12/2003 | Sebastian et al. |
| 2004/0022677 | A1 | 2/2004 | Wohlstadter et al. |
| 2004/0265664 | A1 | 12/2004 | Badding et al. |
| 2005/0112621 | A1 | 5/2005 | Kim et al. |
| 2005/0114045 | A1 | 5/2005 | Giurgiutiu et al. |
| 2005/0199047 | A1 | 9/2005 | Adams et al. |
| 2005/0277852 | A1 | 12/2005 | Shih et al. |
| 2005/0287680 | A1 | 12/2005 | Venkatasubbarao et al. |
| 2006/0053870 | A1 | 3/2006 | Berndt |
| 2006/0217893 | A1 | 9/2006 | Li et al. |
| 2006/0223691 | A1 | 10/2006 | Shih et al. |
| 2006/0228657 | A1 | 10/2006 | Masters et al. |
| 2006/0257286 | A1 | 11/2006 | Adams |
| 2007/0089515 | A1 | 4/2007 | Shih et al. |
| 2007/0141721 | A1 | 6/2007 | Vafai et al. |
| 2007/0169553 | A1 | 7/2007 | Mutharasan |
| 2007/0218534 | A1 | 9/2007 | Klenerman et al. |
| 2008/0034840 | A1 | 2/2008 | Mutharasan |
| 2008/0035180 | A1 | 2/2008 | Mutharasan |
| 2009/0007645 | A1 | 1/2009 | Shih et al. |
| 2009/0053709 | A1 | 2/2009 | Mutharasan |
| 2009/0065742 | A1 | 3/2009 | Shih et al. |
| 2009/0078023 | A1 | 3/2009 | Mutharasan |
| 2009/0203000 | A1 | 8/2009 | Mutharasan |
| 2010/0068697 | A1 | 3/2010 | Shih et al. |
| 2010/0224818 | A1 | 9/2010 | Shih et al. |
| 2010/0239463 | A1 | 9/2010 | Shih et al. |

FOREIGN PATENT DOCUMENTS

| | | |
|---|---|---|
| JP | 3093849 | 4/2000 |
| JP | 2003-298131 | 10/2003 |
| JP | 2004-265899 | 9/2004 |
| JP | 2007-67125 | 3/2007 |
| WO | 98/50773 A2 | 11/1998 |
| WO | 2004/061991 A1 | 7/2004 |
| WO | 2005/043126 A2 | 5/2005 |
| WO | 2006/031072 A1 | 3/2006 |
| WO | 2007/087328 A2 | 8/2007 |
| WO | 2007109228 A1 | 9/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/035732 A3 | 3/2009 |
| WO | 2009/046251 | 4/2009 |

OTHER PUBLICATIONS

Lee, C. et al., "Self-excited piezoelectric PZT microcantilevers for dynamic SFM—with inherent sensing and actuating capabilities", Sensors and Actuators, A72: 179-188 (1999).

Lee, J. H. et al., "Label free novel electrical detection using micromachined PZT monolithic thin film cantilever for the detection of C-reactive protein", Biosensors and Bioelectronics, 20: 269-275 (2004).

Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).

Lee, J. H. et al., "Immunoassay of prostate-specific antigen (PSA) using resonant frequency shift of piezoelectric nanomechanical microcantilever", Biosensors and Bioelectronics, 20: 2157-2162 (2005).

Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).

Lee, Y. et al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).

Li, S. et al., "The intrinsic nature of nonlinear behavior observed in lead zirconate titanate ferroelectric ceramic", J. Appl. Phys., 69(10): 7219-7224 (1991).

Li, X. et al., "Detection of water-ice transition using a lead zirconate titanate/brass transducer", J. Appl. Phys., 92(1): 106-111 (2002).

(56) References Cited

OTHER PUBLICATIONS

Lin, Z. et al., "Operation of an Ultrasensitive 30-MHz Quartz Crystal Microbalance in Liquids", Anal. Chem., 65(11): 1546-1551 (1993).
Liu, W. et al., "Preparation and orientation control of Pb1.1(Zr0.3Ti0.7)O3 thin films by a modified sol-gel process", Mat. Lett., 46: 239-243 (2000).
Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).
Luo, H., "Colloidal Processing of PMN-PT Thick Films for Piezoelectric Sensor Applications", A Thesis Submitted to the Faculty of Drexel University in Jun. 2005.
Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).
Matsui, Y. et al., "Highly Oxidation-Resistant TiN Barrier Layers for Ferroelectric Capacitors", Jpn. J. Appl. Phys., 36(3B): 1586-1588 (1997).
McGovern, J.P. et al., "Real-Time *Salmonella* Detection Using Lead Zirconate Titanate—Titanium Microcantilevers", Mater. Res. Soc. Symp. Proc., 845: AA3.8.1-AA3.8.6 (2005).
Mueller, V. et al., "Nonlinearity and scaling behavior in donor-doped lead zirconate titanate piezoceramic", Appl. Phys. Lett., 72(21): 2692-2694 (1998).
Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).
Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).
Nguyen, L. T. T. et al., "Synthesis and characterization of a photosensitive polyimide precursor and its photocuring behavior for lithography applications", Optical Materials, 29: 610-618 (2007).
Oden, P. I. et al., "Viscous drag measurements utilizing microfabricated cantilevers", Appl. Phys. Lett., 68(26): 3814-3816 (1996).
Ohnmacht, M. et al., "Microcoils and microrelays—an optimized multilayer fabrication process", Sensors and Actuators, 83: 124-129 (2000).
Park, G.T. et al., "Measurement of piezoelectric coefficients of lead zirconate titanate thin films by strain-monitoring pneumatic loading method", Appl. Phys. Lett., 80(24): 4606-4608 (2002).
Park, S.E. et al., "Ultrahigh strain and piezoelectric behavior in relaxor based ferroelectric single crystals", J. Appl. Phys., 82(4): 1804-1811 (1997).
Piezo Systems, Inc., "Piezoceramine Sheets and Their Properties", Piezo Systems, Inc. Catalog: 1-3 (2007).
Pons, T. et al., "Solution-phase single quantum dot fluorescence resonance energy transfer", J. Amer. Chem. Soc., 128(47): 15324-15331 (2006). Abstract Only.
Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).
Ren, W. et al., "Nonlinear behavior of piezoelectric lead zinc niobate-lead titanate single crystals under ac electric fields and dc bias", Appl. Phys. Lett., 83(25): 5268-5270 (2003).
Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.
Saito, Y. et al., "Lead-free piezoceramics", Nature, 432: 84-87 (2004).
Schemmel, A. et al., "Single molecule force spectrometer with magnetic force control and inductive detection", Rev. Sci. Instrum., 70(2): 1313-1317 (1999).
Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).
Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).
Shih, W. et al., "Simultaneous liquid viscosity and density determination with piezoelectric unimorph cantilevers", J. Appl. Phys., 89(2): 1497-1505 (2001).
Shih, W. et al., "Ultrasensitive Pathogen Quantification in Drinking Water Using Highly Piezoelectric Microcantilevers", Amer. Chem. Soc., Chapter 23, 179-185 (2005).
Shih, W. et al., "Nanosensors for Environmental Applications", Nanotechnologies for the Life Sciences, 5: 271-293 (2005).
Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).
Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).
Thundat, T. et al., "Detection of mercury vapor using resonating microcantilevers", Appl. Phys. Lett., 66(13): 1695-1697 (1995).
Tslonsky, M. et al., "Sol-Gel-Derived Ceramic-Carbon Composite Electrodes: Introduction and Scope of Applications", Anal. Chem., 66: 1747-1753 (1994).
Tu, Y. L. et al., "A study of the effects of process variables on the properties of PZT films produced by a single-layer sol-gel technique", J. Mater. Sci., 30: 2507-2516 (1995).
Udayakumar, K. R. et al., "Thickness-dependent electrical characteristics of lead zirconate titanate thin films", J. Appl. Phys., 77(8): 3981-3986 (1995).
Wang, Q.M. et al., "Nonlinear piezoelectric behavior of ceramic bending mode actuators under strong electric fields", J. Appl. Phys., 86(6): 3352-3360 (1999).
Ward, M. D. et al., "In Situ Interfacial Mass Detection with Piezoelectric Transducers", Science, 249: 1000-1007 (1990).
Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).
Ammari, H. et al., "T-Scan Electrical Impedance Imaging System for Anomaly Detection", Siam J. Appl. Math., 65(1): 252-266 (2004).
Baselt, D. R. et al., "Biosensor based on force microscope technology", J. Vac. Sci. Technol. B, 14(2): 789-793 (1996).
Birnie, III, D. P. et al., "Coating uniformity and device applicability of spin coated sol-gel PXT films", Microelectronic Engineering, 29: 189-192 (1995).
Bondoux, C. et al., "MgO insulating films prepared by sol-gel route for SiC substrate", J. Europe. Ceramic Soc., 25: 2795-2798 (2005).
Brito, R. et al., "Adsorption of 3-mercaptopropyltrimethoxysilane and 3-aminopropyltrimethoxysilane at platinum electrodes", J. Electroanalytical Chem., 520: 47-52 (2002).
Capobianco, J. A., et al., "Methyltrimethoxysilane-insulated piezoelectric microcantilevers for direct, all-electrical biodetection in buffered aqueous solutions", Rev. Sci. Instrum., 77: 125105-1-125105-6 (2006).
Capobianco, J. A., et al., "3-mercaptopropyltrimethoxysilane as insulating coating and surface for protein immobilization for piezoeletric microcantilever sensors", Rev. Sci. Instrum., 78: 046106-1-046106-3 (2007).
Carlier, S. G., et al., "Elastography", J. Cardiovasc Risk, 9(5): 237-245 (2002).
Che, G. et al., "Molecular recognition based on (3-mercaptopropyl) trimethoxysilane modified gold electrodes", J. Electroanalytical Chem., 417: 155-161 (1996).
Chen, G. Y. et al., "Adsorption-induced surface stress and its effects on resonance frequency of microcantilevers", J. Appl. Phys., 77(8): 3618-3622 (1995).
Chen, X. et al., "Electrochemical and Spectroscopic Characterization of Surface Sol-Gel Processes", Langmuir, 20(20): 8762-8767 (2004).
Cho, S. H. et al., "Micro-scale metallization on flexible polyimide substrate by Cu electroplating using SU-8 photoresist mask", Thin Solid Films, 475: 68-71 (2005).

(56) References Cited

OTHER PUBLICATIONS

Duval, F.F.C. et al., "Stable TiO2/Pt electrode structure for lead containing ferroelectric thick films on silicon MEMS structures", Thin Solid Films, 444: 235-240 (2003).

Feili, D. et al., "Encapsulation of organic field effect transistors for flexible biomedical microimplants", Sensors and Actuators, A120: 101-109 (2005).

Ferrini, R. et al., "Screening Mammography for Breast Cancer: American College of Preventive Medicine Practice Policy Statement", www.acpm.org/breast, pp. 1-4 (2005).

Fritz, J. et al., "Translating Biomolecular Recognition into Nanomechanics", Science, 288: 316-318 (2000).

Fung, Y. S. et al., "Self-Assembled Monolayers as the Coating in a Quartz Piezoelectric Crystal Immunosensor to Detect *Salmonella* in Aqueous Solution", Anal. Chem., 73: 5302-5309 (2001).

Gao, L. et al., "Imaging of the elastic properties of tissue: A review", Ultrasound in Med. & Biol., 22(8): 959-977 (1996). Abstract Only.

Greenleaf, J. F. et al., "Selected Methods for Imaging Elastic Properties of Biological Tissues", Annu. Rev. Biomed. Eng., 5: 57-78 (2003).

Gu, H. et al., "Single-Calcination Synthesis of Pyrochlore-Free 0.9Pb(Mg1/3Nb2/3)O3-0.1PbTiO3 and Pb (Mg1/3Nb2/3)O3 Ceramics Using a Coating Method", J. Am. Ceram. Soc., 86(2): 217-221 (2003).

Haccart, T. et al., "Evaluation of niobium effects on the longitudinal piezoelectric coeffecients of Pb(Zr,Ti)O3 thin films", Appl. Phys. Lett., 76(22): 3292-3294 (2000).

Han, W. et al., "A magnetically driven oscillating probe microscope for operations in liquids", Appl. Phys. Lett., 69(26): 4111-4113 (1996).

Hiboux, S. et al., "Mixed titania—lead oxide seed layers for PZT growth on Pt(111): a study on nucleation, texture and properties", J. Europe. Ceram. Soc., 24: 1593-1596 (2004).

Hwang, I.H. et al., "Self-actuating biosensor using a piezoelectric cantilever and its optimization", Journal of Physics: Conference Series 34, pp. 362-367, 2006.

Hwang, K.S. et al., "In-situ quantitative analysis of a prostate-specific antigen (PSA) using a nanomechanical PZT cantilever", Lab Chip, 4: 547-552 (2004).

Ilic, B. et al., "Mechanical resonant immunospecific biological detector", Appl. Phys. Lett., 77(3): 450-452 (2000).

Itoh, T. et al., "Self-excited force-sensing microcantilevers with piezoelectric thin films for dynamic scanning force microscopy", Sensor and Actuators, A54:477-481 (1996).

Jung, S.K. et al., "Polymeric Mercaptosilane-Modified Platinum Electrodes for Elimination of Interferants in Glucose Biosensors", Anal. Chem., 68: 591-596 (1996).

Kanda, T. et al., "A flat type touch probe sensor using PZT thin film vibrator", Sensors and Actuators, 83: 67-75 (2000).

Katiyar, P. et al. "Electrical properties of amorphous aluminum oxide thin films", Acta Materialia, 53: 2617-2622 (2005).

Keller, A. et al., "Reliability of Computed Tomography Measurements of Paraspinal Muscle Cross-Sectional Area and Density in Patients With Chronic Low Back Pain", Spine, 28(13): 1455-1460 (2003).

Kelly, J. et al., "Effect of Composition on the Electromechanical Properties of (1-x)Pb(Mg1/3Nb2/3)O3-xPbTiO3 Ceramics" J. Am. Ceram. Soc., 80(4): 957-964 (1997).

Khabari, A. et al., "Partially ionized beam deposition of parylene" J. Non-Crystalline Solids, 351: 3536-3541 (2005).

Kim, S.H. et al., "Influence of Al2O3 diffusion barrier and PbTiO3 seed layer on microstructural and ferroelectric charachteristics of PZT thin films by sol-gel spin coating method," Thin Solid Films, 305: 321-326 (1997).

Kim, S.J. et al., "Fabrication and Characterization of Pb(Zr,Ti)O3 Microcantilever for Resonance Sensors," Jpn. J. Appl. Phys., 42(3): 1475-1478 (2003).

Klissurska, R.D. et al. "Microstructure of PZT sol-gel films on Pt substrates with different adhesion layers," Microelectronic Engineering, 29: 297-300 (1995).

Kruse, S.A. et al., "Tissue characterization using magnetic resonance elastography: preliminary results," Phys. Med. Biol., 45: 1579-1590 (2000).

Kumar, V. et al., "A Simple System for the Preparation of Submicrometer Lead Titanate Powders by the Sol-Gel Method," J. Am. Ceram. Soc., 79(10): 2775-2778 (1996).

Kwok, Clk. et al., "Low temperature perovskite formation of lead zirconate titanate thin films by a seeding process," J. Mater. Res., 8(2): 339-344 (1993).

Weng, L. et al., "Effect of acetylacetone on the preparation of PZT materials in sol/gel processing", Mater. Sci. Engin., B96: 307-312 (2002).

Wilson, L S et al., "Elastography—the movement begins", Phys. Med. Biol., 45: 1409-1421 (2000).

Yi, J. W. et al., "Effect of length, width, and mode on the mass detection sensitivity of piezoelectric unimorph cantilevers", J. Appl. Phys., 91(3): 1680-1686 (2002).

Yi, J. W. et al., "In situ cell detection using piezoelectric lead zirconate titanate-stainless steel cantilevers", J. Appl. Phys., 93(1): 619-625 (2003).

Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.

Zhou, J. et al., "Zeolite-modified microcantilever gas sensor for indoor air quality control," Sensors and Actuators B, Oct. 1, 2003, 94(3), 337-342.

Zhu, D.M. et al., "Thermal conductivity and electromechanical property of single-crystal lead magnesium niobate titanate", Appl. Phys. Lett., 75(24): 3868-3870 (1999).

Data of Commercially Available Product, EDO Corporation: 1-8 (1999).

Data of Commercially Available Product, APC International, Ltd.: 1-2 (2005).

Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).

Campbell, G.A., et al., "Method of measuring Bacillus anthracis spores in the Presence of copious amounts of Bacillus thurigiensis and Bacillus cereus," Anal. Chem. 79, 1145-1152 (2007).

Campbell, G.A., et al., "PEMC sensor's mass change sensitivity is 20 pg/Hz under liquid immersion," Biosensors and Bioelectronics, 22, 35-41 (2006).

Campbell, G.A., et al., "Detection of Bacillus anthracis spores and a model protein usings PEMC sensors in a flow cell at 1 mL/min," Biosensors and Bioelectronics, 22, 78-85 (2006).

Campbell, G.A., et al., "Detection of airborne Bacillus anthracis spores by an integrated system of an air sampler and a cantilever immunosensor," Sensors and Actuators B 127, 376-382 (2007).

Maraldo, et al., "Method for Label-Free Detection of Femtogram Quantities of Biologics in Flowing Liquid Samples," Anal. Chem. 79, 2762-2770 (2007).

Maraldo, et al., "Detection and confirmation of staphylococcal enterotoxin B in apple juice and milk using piezoelectric-excited millimeter-sized cantilever sensors at 2.5 fg/mL," Anal Chem. 79, 7636-7643 (2007).

Maraldo, et al., "Method for Quantification of a Prostate Cancer Biomarker in Urine without Sample Preparation," Anal. Chem. 79, 7683-7690 (2007).

Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).

Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).

Rijal, et al., "PEMC-based method of measuring DNA hybridization at femtomolar concentration directly in human serum and in the presence of copious noncomplementary strands," Anal. Chem., 79, 7392-7400 (2007).

(56) References Cited

OTHER PUBLICATIONS

Rijal, et al., "Method for measuring the Self-Assembly of Alkanethiols on Gold at Femtomolar Concentrations," Langmuir, 23, 6856-6863 (2007).
Wilson, et al., "Viscosity and density values from excitation level response of piezoelectric-excited cantilever sensors," Sensors and Actuators A 138, 44-51 (2007).
Gu, et al., "Single-Calcination Synthesis of Pyrochlore-Free 0.9Pb (Mg1/3Nb2/3)O3-0.1PbTiO3 and Pb(Mg1/3Nb2/3) O3 Ceramics using a Coating Method," J. Am. Ceram. Soc., 86 [2] 217-21 (2003).
Thaysen, et al., "Cantilever-Based Bio-Chemical Sensor Integrated in a Microliquid Handling System," 401-404 (2001).
Li, et al., Micromachined Biomimetic Sensor Using a Modular Artificial Hair Cells, pp. 1-3.
Thaysen, "Label free Detection, BioMEMs Materials and Fabrication Methods," Track 2, 3:00pm, pp. 1-3, Sep. 7, 2002.
R. E. Jaeger and L. Egerton, "Hot-Pressing of Potassium-Sodium Niobates," J. Am. Ceram. Soc. 45, 209 (1962).
H. Birol, D. Damjanovic and N. Setter, "Preparation and Characterization of (K0.5Na0.5)NbO3 Ceramics", J. Eur. Ceram. Soc. 26, 861 (2006).
Y. Guo, K. Kakimoto, and H. Ohsato, "Phase Transitional Behavior and Piezoelectric Properties of (Na0.5K0.5)NbO3—LiNbO3 Ceramics," Appl. Phys. Lett., 85, 4121 (2004).
Y. Guo, K. Kakimoto, and H. Ohsato, "(Na0.5K0.5)NbO3-LiTaO3 Lead-free Piezoelectric Ceramics," Mater. Lett., 59, 241 (2005).
H. Li, W. Y. Shih, and W.-H. Shih, "Effect of Antimony Concentration on the Crystalline Structure, Dielectric and Piezoelectric Properties of (Na0.5K0.5)0.945Li0.055Nb1—xSbxO3 Solid Solutions", J. Am. Ceram. Soc., 90, 3070 (2007).
S. Zhang, R. Xia, T. R. Shrout, J. Zang, and J. Wang, "Piezoelectric Properties in Perovskite 0.948(K0.5Na0.5) NbO3—0.052LiSbO3 lead-free ceramics", J. App. Phys., 100, 104108 (2006).
H. Zhang, et al., "A Sensitive and High-Throughput Assay to Detect Low-Abundance Proteins in Serum," Nature Medicine 12(4) 473-477 (2006).
J. W. Park, S. Kurosawa, H. Aizawa Y. Goda, M. Takai and K. Ishihara, "Piezoelectric Immunosensor for Bisphenol A Based on Signal Enhancing Step With 2-methacrolyloxyethyl Phosphorylcholine Polymeric Nanoparticle," Analyst, 131, 155-162 (2006).
A. M. Smith, G. Ruan, M. N. Rhyner, and S. Nie, "Engineering Luminescent Quantum Dots for In Vivo Molecular and Cellular Imaging," Ann. Biomed. Eng., 34 (1),3-14 (2006).
Y. Guo, K. Kakimoto, and H. Ohsato, "Phase Transitional Behavior and Piezoelectric Properties of (Na0.5K0.5)NbO3-LiNbO3 Ceramics," Appl. Phys. Lett., 85, 4121 (2004).
H. Li, W. Y. Shih, and W.-H. Shih, "Effect of Antimony Concentration on the Crystalline Structure, Dielectric and Piezoelectric Properties of (Na0.5K0.5)0.945Li0.055Nb1-xSbxO3 Solid Solutions", J. Am. Ceram. Soc., 90, 3070 (2007).
S. Zhang, R. Xia, T. R. Shrout, J. Zang, and J. Wang, "Piezoelectric Properties in Perovskite 0.948(K0.5Na0.5)NbO3-0.052LiSbO3 lead-free ceramics", J. App. Phys., 100, 104108 (2006).
X. Li, W. Y. Shih, J. S. Vartuli, D. L. Milius, I. A. Aksay, and W.-H. Shih, "Effect of Transverse Tensile Stress on Electric-Field-Induced Domain Reorientation in Soft PZT: In Situ XRD Study", J. Am. Ceram. Soc. 85 (4), 844 (2002).
Q. Zhu, W. Y. Shih, and W.-H. Shih, "Real-Time, Label-Free, All-Electrical Detection of *Salmonella typhimurium* Using Lead Titanate Zirconate/Gold-Coated Glass Cantilevers at any Relative Humidity," *Sensors and Actuators* B, 125, 379-388 (2007).
Q. Zhu, W. Y. Shih, and W.-H. Shih, "Length and Thickness Dependence of Longitudinal Flexural Resonance Frequency Shifts of a Piezoelectric Microcantilever Sensor due to Young's Modulus Change," *J. Appl. Phys.* 104, 074503 (2008).
Q. Zhu, W. Y. Shih, and W.-H. Shih, "Enhanced Detection Resonance Frequency Shift of a Piezoelectric Microcantilever Sensor by a DC Bias Electric Field in Humidity Detection," Sensors and Actuators, B 138, 1 (2009).
Q. Zhu, W. Y. Shih, and W.-H. Shih, "Mechanism of the Flexural Resonance Frequency Shift of a Piezoelectric Microcantilever Sensor in a DC Bias Electric Field," *Appl. Phys. Lett.* 92, 033503 (2008).
Q. Zhu, Drexel University (2008).
McGovern, J.P. Drexel University (2008).
Luo, H.Y. Drexel University (2005).
Shin, S., Kim, J.P., Sim, S.J. & Lee, J. A multisized piezoelectric microcantilever biosensor array for the quantitative analysis of mass and surface stress. *Applied Physics Letters* 93,—(2008).
Pang, W. et al. Femtogram mass sensing platform based on lateral extensional mode piezoelectric resonator. *Applied Physics Letters* 88,—(2006).
Cherian, S. & Thundat, T. Determination of adsorption-induced variation in the spring constant of a microcantilever. *Applied Physics Letters* 80, 2219-2221 (2002).
Haun, M.J. "Thermodynamic Theory of the Lead Zirconate-Titanate Solid Solution System," The Pennsylvania State University (1988).
Lee, J.H. et al. Immunoassay of prostate-specific antigen (PSA) using resonant frequency shift of piezoelectric nanomechanical microcantilever. *Biosensors and Bioelectronics* 20, 2157-2162 (2005).
E. Chen, "Ultrasound Tissue Displacement and Tissue Elasticity Imaging," Ph.D. dissertation, University of Illinois at Urbana-Champaign, (1995).
Zhu, Q., Shih, W.Y. & Shih, W.-H. In situ, in-liquid, all-electrical detection of *Salmonella typhimurium* using lead titanate zirconate/gold-coated glass cantilevers at any dipping depth. *Biosensors and Bioelectronics* 22, 3132-3138 (2007).
McGovern, J.P. et al. Label-free flow-enhanced specific detection of Bacillus anthracis using a piezoelectric microcantilever sensor. *Analyst* 133, 649-654 (2008).
McGovern, J.P., Shih, W.Y. & Shih, W.H. In situ detection of Bacillus anthracis spores using fully submersible, self-exciting, self-sensing PMN-PT/Sn piezoelectric microcantilevers. *Analyst* 132, 777-783 (2007).
McGovern, J.-P. et al. Label-free flow-enhanced specific detection of Bacillus anthracis using a piezoelectric microcantilever sensor. *The Analyst* 133, 649-654 (2008).
McGovern, J.-P., Shih, W.Y. & Shih, W.-H. In situ detection of Bacillus anthracis spores using fully submersible, self-exciting, self-sensing PMN-PT/Sn piezoelectric microcantilevers. *The Analyst* 132, 777-783 (2007).
Zhu, Q., Shih, W.Y. & Shih, W.-H. Mechanism of flexural resonance frequency shift of a piezoelectric microcantilever sensor during humidity detection. *Applied Physics Letters* 92, 183505-3 (2008).
Su, W.-S., Chen, Y.-F., Shih, W.Y., Luo, H. & Shih, W.-H. Domain switching in lead magnesium niobate-lead titanate polycrystalline sheets at single grain level. *Applied Physics Letters* 91, 112903-3 (2007).
Shang, J.K. & Tan, X. Indentation-induced domain switching in Pb(Mg1/3Nb2/3)O3—PbTiO3 crystal. *Acta Materialia* 49, 2993-2999 (2001).
Alguero, M., Jimenez, B. & Pardo, L. Rayleigh type behavior of the Young's modulus of unpoled ferroelectric ceramics and its dependence on temperature. *Applied Physics Letters* 83, 2641-2643 (2003).
Masys, A.J., Ren, W., Yang, G. & Mukherjee, B.K. Piezoelectric strain in lead zirconate titante ceramics as a function of electric field, frequency, and dc bias. *Journal of Applied Physics* 94, 1155-1162 (2003).
Capobianco, J.A., Shih, W.Y., Yuan, Q.-A., Adams, G.P. & Shih, W.-H. Label-free, all-electrical, in situ human epidermal growth receptor 2 detection. *Review of Scientific Instruments* 79, 076101 (2008).
Shih, W.Y., Luo, H., Li, H., Martorano, C. & Shih, W.-H. Sheet geometry enhanced giant piezoelectric coefficients. *Applied Physics Letters* 89, 242913-3 (2006).
Q. Ren and Y. P. Zhao, "Influence of surface stress on frequency of microcantilever-based biosensors," Microsystem Technologies, 2004, pp. 307-314, vol. 10.
Morton, T.A., Myszka, D.G. & Chaiken, I.M. Interpreting Complex Binding-Kinetics from Optical Biosensors—a Comparison of Analysis by Linearization, the Integrated Rate-Equation, and Numerical-Integration. *Analytical Biochemistry* 227, 176-185 (1995).
Shuck, P. & Minton, A.P. Kinetic analysis of biosensor data: elementary test of self-consistency. *Trends Biochemical Sciences* 21, 458-460 (1996).

(56) References Cited

OTHER PUBLICATIONS

McKendry, R. et al. Multiple label-free biodetection and quantitative DNA-binding assays on a nanomechanical cantilever array. *Proceedings of the National Academy of Sciences of the United States of America* 99, 9783-9788 (2002).

Ndieyira, J.W. et al. Nanomechanical detection of antibiotic mucopeptide binding in a model for superbug drug resistance. *Nature Nanotechnology* 3, 691-696 (2008).

Sofian M. Kanan and Carl P. Tripp, "An Infrared Study of Adsorbed Organophosphonates on Silica: A Prefiltering Strategy for the Detection of Nerve Agents on Metal Oxide Sensors," Langmuir 2001, 17, 2213-2218, United States of America.

"Enhanced detection resonance frequency shift of a piezoelectric microcantilver sensor by a DC bias electric field in humidity detection," Sensors and Actuators B: Chemical, 2009, vol. 138, United States of America.

J. K. Shang and X. Tan, "Indentation-Induced Domain Switching in Pb(Mg1/3Nb2/3)O3—PbTiO3 Crystal" Acta Mater., 2001, pp. 2993-2999, vol. 49, Urbana, Illinois.

IEEE Standard on Piezoelectricity IEEE, New York, 1988, Chap. 6.

L. Bellaiche and David Vanderbilt, Physical Review Letters, 83(7), Aug. 16, 1999, 1347.

S-F. Liu, W. Ren, B. K. Mukherjee, S. J. Zhang, T. R. Shrout, P. W. Rehrig, and W. S. Hackenberger, Appl. Phys. Lett., 83, 2886 (2003). PZT data, IEEE Micro Electro Mechanical Systems Workshop, Jan.-Feb. 1991, Nara, Japan p. 118.

Xu, et al., "Longtitudinal piezoelectric coefficient measurement for bulk ceramics and thin films using pneumatic pressure rig," Journal of Applied Physics, Jul. 1, 1999, pp. 588-594, vol. 86, No. 1, Pennsylvania.

Li, "Sodium Potassium Niobate-based Lead-free Piezoelectric Ceramics: Bulk and Freestanding Thick Films," Thesis Submitted to Faculty of Drexel University, Jun. 2008, Philadelphia, Pennsylvania.

Li, "Synthesis of Na0.5K0.5NbO3 Piezoelectrics by a Solution Coating Approach," Int. J. Appl. Technol., 2009, pp. 205-215, vol. 6, Issue 2, United States of America.

Hudson, J.B. Surface Science: An Introduction, (Wiley-IEEE, New York, 1998).

Q. Zhu. "Enhanced detection resonance frequency shift of a piezoelectric microcantilever sensor by a DC bias electric field in humidity detection," Sensors and Actuators B: Chemical, 2009, pp. 1-4, vol. 138.

Q. Zhu, W. Y. Shih & W.H. Shih, "Mechanism of flexural resonance frequency shift of a piezoelectric microcantilever sensor during humidity detection," Applied Physics Letters, 2008, vol. 92, United States of America.

Hudson, J.B. Surface Science: An Introduction, Wiley-IEEE, 1998, pp. 96-98, New York.

Leckband, D.E. et al. Force Probe Measurements of Antibody-Antigen Interactions. Methods 20, 329-340 (2000).

O'Sullivan, C.K. & Guilbault, G.G. Commercial quartz crystal microbalances—theory and applications. Biosensors & Bioelectronics 14, 663-670 (1999).

Lofgren, J.A. et al. Comparing ELISA and surface plasmon resonance for assessing clinical immunogenicity of panitumumab. J Immunol 178, 7467-72 (2007).

Borghaei, et al., "induction of Adaptive Anti-HER2/neu Immune Responses . . . " J. Immunother, Jun. 2007, pp. 455, vol. 30, No. 4.

H. Yengingil, "Breast Cancer Detection and Differentiation Using Piezoelectric Fingers," PhD Thesis, Drexel University, Philadelphia, PA, Jan. 2009.

E. E. Konofagou, T. Harrigan, and J. Ophir, "Shear Strain Estimation and Lesion Mobility Assessment in Elastography," Ultrasonics, 2000, pp. 400-404, vol. 38.

H.O. Yegingil, W. Y. Shih, W. Anjum, A. D. Brooks and W.-H. Shih, "Soft tissue elastic modulus measurement and tumor detection using piezoelectric fingers," Mat. Res. Soc. Symp. Proc., 2006, vol. 898E. Sure Touch Exam [online] retrieved Nov. 29, 2010 from the internet @ http://www.medicaltactile.com/default.htm.

Z. Shen, W. Y. Shih, and W.-H. Shih, "Mass detection sensitivity of piezoelectric cantilevers with a nonpiezoelectric extension," Rev. Sci. Instrum. 77, 065101 (2006).

A. Markidou, W. Y. Shih, and W.-H. Shih, "Soft-materials elastic and sear moduli measurement using piezoelectric cantilevers," Rev. Sci. Ins. 76, 064302 (2005).

S . T. Szewczyk, W.Y. Shih, and W.-H. Shih, "Palpationlike soft-material elastic modulus measurement using piezoelectric cantilievers," Rev. Sci. Ins., 77, 044302 (2006).

H. O. Yegingil, W. Y. Shih, and W.-H. Shih, "All-electrical indentation shear modulus and elastic modulus measurement using a piezoelectric cantilever with a tip," J. Appl. Phys., 101, 054510 (2007).

W. Jiang and W. Cao, "Intrinsic and coupling-induced elastic nonlinearity of lanthanum-doped lead magnesium niobate-lead titanate electrostrictive ceramic," Appl. Phys. Lett., 77,1387 (2000).

A. W. McFarland, et al., "Influence of surface stress on the resonance behavior of microcantilevers," Appl. Phys. Lett. 87, 053505 (2005).

O. Kwon, "T-scan Electrical Impedance Imaging system for anomaly detection," Siam J. Appl. Math., 2004, pp. 252-266, vol. 65, No. 1.

Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39, May 24, 2006.

Campbell, G.A., et al., "Detection and quantification of proteins using self-excited PZT-glass millimeter-sized cantilever," Biosensors and Bioelectronics, 26-36, Dec. 20, 2004.

Campbell, G.A., "Piezoelectric-excited millimeter-sized cantilever (PEMC) sensors detect *Bacillus anthracis* at 300 spores/mL," Biosensors and Bioelectronics, 37-45, Mar. 15, 2006; 21(9):1684-92.

Campbell, G.A., et al., "Kinetics of bacillus anthracis spore binding to antibody functionalized PEMC sensors in presence of *bacillus thuringiensis* and *bacillus cereus* ," J. Publications, Am. Chem. Soc. 25 pages, (Mar. 2007); 79 (3):1145-52.

Campbell, G.A., et al., "*Escherichia coli* O157:H7 detection limit of millimeter-sized PZT cantilever sensors in 700 cells/mL," Analytical Sci., 11-13, vol. 21 (2005) No. 4 pp. 355-357.

Campbell, G.A., et al., "Detection of pathogen *Escherichia coli* O157:H7 using self-excited PZT-glass microcantilevers," Biosensors and Boelectronics, 14-25, Sep. 15, 2005, pp. 462-473.

Campbell, G.A., "Detection of *staphylococcus* enterotoxin B at pictogram levels using piezoelectric-excited millimeter-sized cantilever sensors," Submitted on line to J. of Analytical Chem., 1-24, (Mar. 29, 2006).

Campbell, G.A., et al., "Detect *Escherichia coli* O157:H7 in ground beef samples using piezoelectric excited millimeter-sized cantilever (PEMC) sensors," Submitted on-line to Biosensors and Bioelectronics, 2-34, (2007).

Campbell, G.A., et al., "A method for measuring *Escherichia coli* O157:H7 at 1 cell/mL in 1 liter sample using antibody functional piezoelectric-excited millimeter sized cantilever sensor," Paper submitted on-line to J. of Analytical Chemistry. 1-23, Jan. 23, 2007.

Carr, D.W., et al., "Fabrication of nanoelectromechanical systems in single crystal silicon using silicon on insulator substrates and electron beam lithography," J. Vac. Sci. Technology, B, 5(6), 2760-2763, Nov. 1997.

Wellman, P. S. et al., "Tactile Imaging of Breast Masses", Arch. Surg., 136: 204-208 (2001).

Wilson, L. "Pezoelectric-excited millimeter-sized cantilever (PEMC) sensor provides viscosity and density measurements." Submitted to Review of Scientific Instruments (2005): 1-26.

Li, et al., Micromachined Biomimetric Sensor Using a Modular Artificial Hair Cells, pp. 1-3 (2000).

Luo, H. et al., "Synthesis of PMN and 65PMN-35PT Ceramics and Films by a New Suspension Method", Ceramic Transactions, 136, pp. 251-260, (2003).

Maraldo, D. et al., "Resonant-mode millimeter sized cantilever biosensor for continuous detection of proteins and pathogens in flowing liquids," Dept. of Chem. and Biological Eng., 1-21 (2006).

Mazza, E. et al., Biomechanics, http://www.zfm.ethz.ch/e/resibio/, 1-10, (Feb. 24, 2009).

Wang, Y., et al. "Tactile mapping of palpable abnormalities for breast cancer diagnosis." Robotics and Automation, 1999. Proceedings. 1999 IEEE International Conference on. vol. 2. IEEE, 1999.

Wellman, P., et al. "Breast tissue stiffness in compression is correlated to histological diagnosis." Harvard BioRobotics Laboratory Technical Report (1999).

* cited by examiner

PIEZOELECTRIC MICROCANTILEVER SENSORS FOR BIOSENSING

This application is a divisional of U.S. patent application Ser. No. 12/514,941 filed Nov. 18, 2009, which is a 371 of International Patent Application No. PCT/US2007/085771, filed Nov. 28, 2007, which in turn claims the benefit of U.S. Provisional Patent Application No. 60/867,538 filed Nov. 28, 2006.

STATEMENT OF GOVERNMENT INTEREST

This invention was reduced to practice with Government support under Grant No. R01 EB000720 awarded by the National Institutes of Health; the Government is therefore entitled to certain rights to this invention.

BACKGROUND OF THE INVENTION

1. Field of the Invention

The invention relates to piezoelectric microcantilever sensors for biosensing. More specifically, the invention relates to highly sensitive piezoelectric microcantilevers capable of determining the presence and/or mass of organic compounds. Applicable fields of use may include biodefense, food safety and pathogen detection.

2. Description of the Related Technology

Current biosensing technologies utilize quartz crystal microbalances (QCM), silicon microcantilevers, electrochemical enzyme immunoassays, fluorescence, laser-based or fiber-optics-based methods, amplification schemes such as polymerase chain reaction (PCR), or bound metal particles to determine the presence and/or mass of organic compounds. These techniques, however, fail to provide quantitative, efficient or highly sensitive detection. In addition to lacking sensitivity, they are also incapable, in some cases, of simultaneously monitoring multiple compounds or being used in high throughput array applications.

TABLE 1

Comparison of PEMS with Other Biosensors

| Detector Type | Detection sensitivity | Label-free | Direct, In-situ | Rapid | High-throughput | Multiplexing |
|---|---|---|---|---|---|---|
| PEMS | $10^{-15}$-$10^{-18}$ g | yes | yes | yes | yes | yes |
| QCM | $10^{-9}$ g | yes | yes | Yes | No | no |
| Silicon microcantilever | $10^{-12}$ g | yes | no | No | No | no |
| Optical fiber fluorescence |  | no | no | No | Yes | yes |
| ELISA[26] | $10^{-10}$ g | no | no | No | Yes | yes |
| SPR[3] | $10^{-12}$ g | yes | yes | Yes | No | no |

Of these technologies, QCM, which utilizes thickness-mode resonance sensing, is one of the most common commercially available biosensing technologies. Detection sensitivity of a QCM is related to the resonance frequency and the thickness of the quartz membrane. A resonance frequency of about 5 MHz, corresponding to a quartz membrane thickness of 330 μm, enables a minimum detectable mass density of about $10^{-9}$ g/cm$^2$. Sensitivity is therefore generally limited to a range of about $10^{-8}$ g/Hz.

To increase sensitivity, some biosensors utilize silicon-based microcantilevers, which offer a sensitivity of approximately $10^{-12}$ g/Hz, about three orders of magnitude higher than QCMs. Advantageously, silicon microcantilevers are also widely available and may be easily integrated with existing silicon fabrication methodologies. Most silicon microcantilevers, however, rely on complex external optical components for deflection detection, an external driving mechanism for actuation and also require laser alignment. Moreover, because they are not piezoelectric, silicon microcantilevers are inferior for in-solution sensing, yielding low resonance peaks upon immersion in a solution.

Piezoelectric cantilevers, in comparison, use electrical means for detection and are not encumbered by the complexity and mass of the silicon-based sensors. Constructed from lead zirconate titanate (PZT), they are capable of electrical self-excitation and self-sensing for in-situ electrical detection. Currently, piezoelectric biosensors are millimeter-size cantilevers made by bonding commercial PZT to non-piezoelectric substrates such as stainless steel, titanium or glass. Although capable of in-situ biosensing, these millimeter-size cantilevers lack the desired sensitivity for such applications.

Thin-film-based PZT microcantilevers, such as those disclosed in JP-07027559 A2 and U.S. Pat. No. 7,084,554, are highly sensitive instruments. U.S. Pat. No. 7,084,554, in particular, discloses a thin piezoelectric film biomorph capable of being formed as a cantilever. The biomorph may be composed of a piezoelectric thin PZT film of about 1-10 μm in thickness for the purpose of increasing the working frequency range of micro-electro-mechanical dimensioned (MEMS) systems. The patent further teaches that the piezoelectric thin film may be fabricated by thin film fabrication methods such as a sol-gel method, sputtering, hydrothermal methods, chemical vapor deposition (CVD) or another thin film fabrication method, followed by low temperature annealing and dry etching, plasma etching or patterning by wet chemical etching (See col. 5, lines 55-64 of U.S. Pat. No. 7,084,554). These piezoelectric microcantilevers, however, are incapable of in-situ electrical detection due to degradation of resonance peaks in solution.

Recent advances in thin-film PZT microcantilevers incorporate an electrical insulation layer that prevents liquid damping. U.S. Patent Publication no. 2005/0112621 discloses an insulation layer surrounding a PZT microcantilever having a thin piezoelectric film in order to prevent conduction in liquid media (See e.g. col. 4, lines 28-36).

However, there remains a need for a piezoelectric microcantilever device capable of in-solution biologic detection having a femtogram or higher sensitivity. In addition, there remains a need for a device consisting of array piezoelectric microcantilevers that is capable of simultaneous detection of multiple compounds.

Advancement in the sensitivity, accuracy and efficiency of electrical biosensing is essential to the developing field of bioterrorism defense. During the fall of 2001, for example, *bacillus Anthracis* spores, a bioterrorism agent, were responsible for the deaths of 5 individuals and infection of 17 others. As bioterrorism threats become more prevalent, there is a growing need for reliable in-situ detectors capable of efficiently detecting multiple biological agents in real time.

Advancements in biosensing accuracy, sensitivity, multi compound detection are also potentially useful in the health sciences for early detection and prevention of diseases. Breast cancer, for example, is the second leading cause of death for women. Although a number of potential breast cancer markers, such as HER2 (HER2/neu, c-erbB-2), EGFR, CA-15-3, CA27.29, urokinase plasminogen activator receptor (uPAR), carcinoembryonic antigen (CEA), α-fetoprotein (AFP), and cytokeratins, are known, no blood test or method for detecting these markers currently exists. Mammography is frequently inadequate and often produces false positives leading to unnecessary biopsies. Therefore early detection methods for various cancers and other diseases lacking adequate diagnostic means, like breast cancer, that are capable of accurately, effectively and non-invasively identifying and quantifying pathogens and other disease markers are also needed.

SUMMARY OF THE INVENTION

In a first aspect, the present invention is directed to piezoelectric microcantilever sensors useful for detecting organic compounds. The piezoelectric microcantilever includes a piezoelectric layer, a non-piezoelectric layer and a receptor. The microcantilever may be constructed from piezoelectric lead magnesium niobate-lead titanate $(Pb(Mg_{1/3}Nb_{2/3})O_3)_{0.65}$—$(PbTiO_3)_{0.35}$ $(PMN_{0.65}$—$PT_{0.35})(PMN$—$PT)$ which typically has a thickness not greater than 70 μm with a dielectric constant of at least 1600.

In a second embodiment, the piezoelectric layer of the microcantilever is constructed from lead zirconate titanate (PZT), which typically has a thickness not greater than 4 μm with a dielectric constant of at least 1600.

In another aspect, the present invention is directed to methods for bioterrorism defense, food safety and pathogen detection.

DETAILED DESCRIPTION OF THE PREFERRED EMBODIMENTS

Piezoelectric microcantilever sensors (PEMS) are mass sensors that use an electrical means for detection. Receptors are coated on the surface of PEMS to bind molecules of interest. The PEMS detects a change in mass because newly bound target molecules shift the mechanical resonance frequency of the device. By monitoring the resonance frequency shifts, a PEMS is capable of rapid, label-free, in situ quantitative detection of organic compounds or molecules including pathogens, antigens and proteins in a small volume solution (e.g. 100 μl) or in a cell culture using simple all-electrical measurements. PEMS are capable of electric actuation and detection and may also be constructed as an array for simultaneous monitoring of multiple target compounds or molecules.

Figure 1:
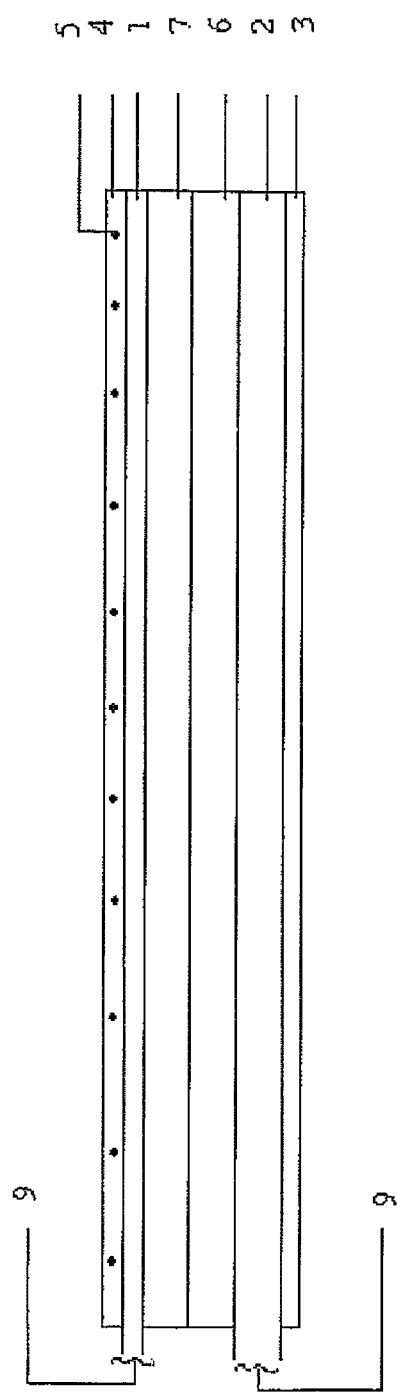
FIG. 1 is a cross section of one embodiment of a piezoelectric microcantilever in accordance with the present invention.

FIG. 1 shows the basic structure of a microcantilever sensor. A PEMS includes a conductive element 1 and a second conductive element 2 (bottom electrode), electrically insulating layer 3, receptor immobilization layer 4, receptors 5, at least one non-piezoelectric layer 6, and at least one piezoelectric layer 7. The PEMS shown in FIG. 1 also includes electrical leads 9.

Conductive elements 1, 2 may be any element capable of conducting an electrical signal from the piezoelectric layer to a device for detecting that signal. In a preferred embodiment, conductive elements 1 and 2 are electrodes which may be constructed from any conductive material. Preferably, the first electrode 1 is constructed from Au/Cr or Pt/Ti and subsequently patterned in several regions. The second electrode 2 is preferably constructed from Pt/TiO$_2$ on SiO$_2$ for PZT/SiO$_2$ PEMS or Pt/Ti on a metal substrate or non-piezoelectric layer and subsequently patterned as well.

In order to maintain functionality in solution by preventing conduction, it may be useful to electrically separate or buffer conductive element 1 and second conductive element 2. Conductive element 1 is patterned slightly smaller than the piezoelectric layer 7 to ensure complete insulation of the edges and corners thereof. Any electrically insulating layer 3 may be used as a coating to achieve electrical separation or buffering.

In one embodiment, insulating layer 3 may comprise a 1.5 μm thick parylene (poly-para-xylylene) coating deposited on an electrode by chemical vapor deposition. When placed in static and 1 ml/min flow rate of PBS solution, a parylene insulating layer 3 essentially prevents background resonance frequency shifts greater than 30 Hz and 60 Hz, respectively, over a period of 30 minutes. As a result, insulating layer 3 enables complete submersion of the microcantilever for in situ or in-solution detection while maintaining a Q value (quality value) greater than 35. For the purposes of this patent application, Q value is defined as the ratio of the resonance frequency to the resonance peak width at half the peak height.

Alternatively, a PEMS may be insulated using self-assembled monolayers with hydrophobic properties, preferably methyltrimethoxysilane (MTMS) or a combination of MTMS with parylene coatings of varying thicknesses, may also be used. When immersed in a PBS solution, an MTMS insulated piezoelectric microcantilever yields strong resonance peak intensities and prevents background resonance frequency shifts greater than 30 Hz over a period of 30 minutes.

Other insulation materials may include 3-mercaptopropyl trimethoxysilane, Al$_2$O$_3$, SiO$_2$ and any functional hydrophobic silane, having a hydrophobic group selected from the group consisting of alkyl, phenyl, alkyl halide, alkene, alkyne, and sulfhydryl. In a preferred embodiment, the insulation material is mercaptopropylsilane (MPTS), which can also function to immobilize a receptor on the cantilever. The insulating materials may also include any combination of any of MTMS, MPTS, parylene, 3-mercaptopropyl trimethoxysilane, Al$_2$O$_3$, SiO$_2$, any functional hydrophobic silane having a hydrophobic group selected from the group consisting of alkyl, phenyl, alkyl halide, alkene, alkyne, and sulfhydryl, or a combination thereof.

Receptors 5 may be densely packed and immobilized onto, for example, a bi-functional linker modified sensor surface. Any receptor, such as specially synthesized cavitants, DNA oligonucleotides, proteins, single chain variable fragments (scFvs), enzymes, and antibodies to cells, antigens, pathogens, viruses, parasites, or combinations thereof may be bound to the sensor surface. For example, when trying to detect tumors, monomeric and dimeric anti-tumor scFv molecules, which are composed of variable light and heavy chains of antibody molecule anti-ECD scFV, that react to cancer markers may be bound to the electrodes. Similarly, when trying to detect *Bacillus anthracis* ("BA"), antibodies specific to BA spore surface antigens may be immobilized on the electrodes.

Any means of adhering receptors 5 to the sensor surface may be utilized. In a preferred embodiment, receptors 5 are bound to the electrodes using an immobilization coating 4, such as self assembled monolayers ("SAM"), MPTS and bi-functional linkers. In one embodiment, for purposes of binding scFv, the immobilization coating may be a self assembled monolayer of 3-mercaptoproprionic acid (MPA) on a copper and gold-coated electrode activated with 1-ethyl-3-(3-dimethylaminopropy)carbodimide hydrochloride (EDC) and 5 mg/ml N-hydroxysulfosuccinimide (NHS).

The PEMS also includes at least one non-piezoelectric layer 6, which may be fabricated from any compatible material, including a ceramic material, a polymeric material, a metallic material or combinations thereof. Preferably the non-piezoelectric layer 6 is fabricated from silicon dioxide (SiO$_2$) and silicon nitride (Si$_3$N$_4$) for PZT-thin film based PEMS. For example, a silicon nitride coating on single crystal silicon wafer may be prepared by low press chemical vapor deposition. A low stress silicon dioxide layer may subsequently be deposited on the silicon nitride layer by growing silicon dioxide films using low temperature oxide deposition or plasma enhanced chemical vapor deposition. For PMN—PT-based PEMS, the non-piezoelectric layer can be any ceramic, metallic, or polymeric layer. A metallic layer such as Cu, tin, Ni, Ti, etc., or any combination is preferred because it can be provided by simple electroplating.

Non-piezoelectric layer 6 may be bonded to a shorter piezoelectric layer 7 so that the portion of non-piezoelectric layer 6 extending beyond the end of piezoelectric layer 7 forms a non-piezoelectric tip. Both piezoelectric layer 7 and non-piezoelectric layer 6 may be attached to a clamp. In an alternative embodiment, piezoelectric layer 7 may extend beyond non-piezoelectric layer 6, forming a piezoelectric tip. Optionally, the PEMS may be constructed so that neither piezoelectric layer 7 nor the non-piezoelectric layer 6 extends beyond the other. In order to achieve the best results, one of the piezoelectric 7 and non-piezoelectric layers 6 preferably extends beyond the other to form a tip. A PEMS may also include multiple piezoelectric and non-piezoelectric layers. For example, a non-piezoelectric layer may be placed between two piezoelectric layers or a piezoelectric layer may be placed between two non-piezoelectric layers.

A significant aspect of the microcantilever device is the fabrication of a highly piezoelectric layer 7, which enables electrical detection and actuation within the cantilever. The piezoelectric layer may function as a driving element, vibrating element and sensing element. Applying an AC voltage (input) across the piezoelectric layer bends and vibrates the PEMS, which in turn induces a piezoelectric voltage that produces readily detectable changes in the magnitude and phase of the output voltage. The resonance frequency of the PEMS is obtained by monitoring the maximum of the phase shift of the output voltage. This measurement is accomplished all-electrically, i.e., electrical actuation and electrical sensing.

Piezoelectric layer 7 may be constructed from any piezoelectric material, including a lead-free piezoelectric material such as $(Na_{0.5}K_{0.5})_{0.945}Li_{0.055}Nb_{0.96}Sb_{0.04}O_3$ (hereinafter "Sb—NKNLN"), $Sb—(Na_{0.5}K_{0.5})NbO_3—LiTaO_3$ (hereinafter "Sb—NKNLT"), $Sr—(Na_{0.5}K_{0.5})NbO_3—LiTaO_3$ (Sr—NKNLN), $Sr—Na_{0.5}K_{0.5})NbO_3—LiTaO_3$ (Sr—NKNLT), $SbSr—(Na_{0.5}K_{0.5})NbO_3—LiTaO_3$ (SrSb—NKNLN), $SrSb—Na_{0.5}K_{0.5})NbO_3—LiTaO_3$ (SbSr—NKNLT), solid solutions with $(Bi_{0.5}K_{0.5})TiO_3$, $(Bi_{0.5}Na_{0.5})TiO_3$, $Ba(Zr_xTi_{1-x})O_3$, $BaTiO_3$ (hereinafter "BT"), $(Bi_{1/2}K_{1/2})TiO_3$ (hereinafter "BKT"), $(Bi_{1/2}Na_{1/2})TiO_3$ (hereinafter "BNT"), $Ba(Zr_xTi_{1-x})O_3$ (hereinafter "BZT"), $Bi(Zn_{1/2}Ti_{1/2})O_3$ (hereinafter "BiZT"), $(Na_xK_{1-x})NbO_3$ (hereinafter "NKN"), $BiScO_3—PbTiO_3$ $BaTiO_3—(Bi_{1/2}K_{1/2})TiO_3$ (hereinafter "BKBT"), $(Bi_{1/2}Na_{1/2})TiO_3—(Bi_{1/2}K_{1/2})TiO_3$ (hereinafter "BNKT"), $(Bi_{1/2}Na_{1/2})TiO_3—BaTiO_3$ (hereinafter "BNBT"), $(Bi_{1/2}Na_{1/2})TiO_3—Ba(Zr_xTi_{1-x})O_3$ (hereinafter "BNBZT") and $(Bi_{1/2}Na_{1/2})TiO_3—BaTiO_3—(Bi_{1/2}K_{1/2})TiO_3$ (hereinafter "BNBK").

In a preferred embodiment, the piezoelectric layer is fabricated from highly piezoelectric lead magnesium niobate-lead titanate films, e.g. $(Pb(Mg_{1/3}Nb_{2/3})O_3)_{0.65}—(PbTiO_3)_{0.35}$ ($PMN_{0.65}—PT_{0.35}$)(PMN—PT), highly piezoelectric lead zirconate titanate (PZT) films or high piezoelectric lead-free films. Additionally, piezoelectric layer 7 may be fabricated in any form, preferably having free standing film geometry to enhance domain wall motion and piezoelectric performance.

A piezoelectric PMN—PT layer may be fabricated using a precursor-suspension method. Submicron crystalline PMN powder is first prepared by dispersing $Mg(OH)_2$-coated $Nb_2O_5$ particles in a lead acetate/ethylene glycol solution followed by calcination at about 800° C. The crystalline PMN powder was subsequently suspended in a lead titanate (PT) precursor solution containing lead acetate and titanium isopropoxide in ethylene glycol to form a PMN—PT precursor powder, which can be sintered at a temperature as low as about 900° C.

The resulting suspensions have previously been used to formulate PMN—PT freestanding films of about 8-75 μm thick upon sintering at 1000° C. Preferably, the thickness is about 1 μm-127 μm, more preferably less than about 50 μm, and most preferably less than about 8 μm. The precursor-suspension method may also be used to produce freestanding PMN—PT films having a thickness of less than 8 μm or larger than 75 μm. Typically, the freestanding PMN—PT films have femtogram sensitivity of at least $2×10^{-14}$ g/Hz, dielectric constants greater than 1000, saturated polarization of about 30 μC/cm², remnant polarization of 25 μC/cm² and a Q value as high as 300 and as low as 20. Therefore PMN—PT microcantilevers are capable of generating higher-mode resonance peaks resulting in enhanced sensitivity detection.

Figures 2A, 2B:
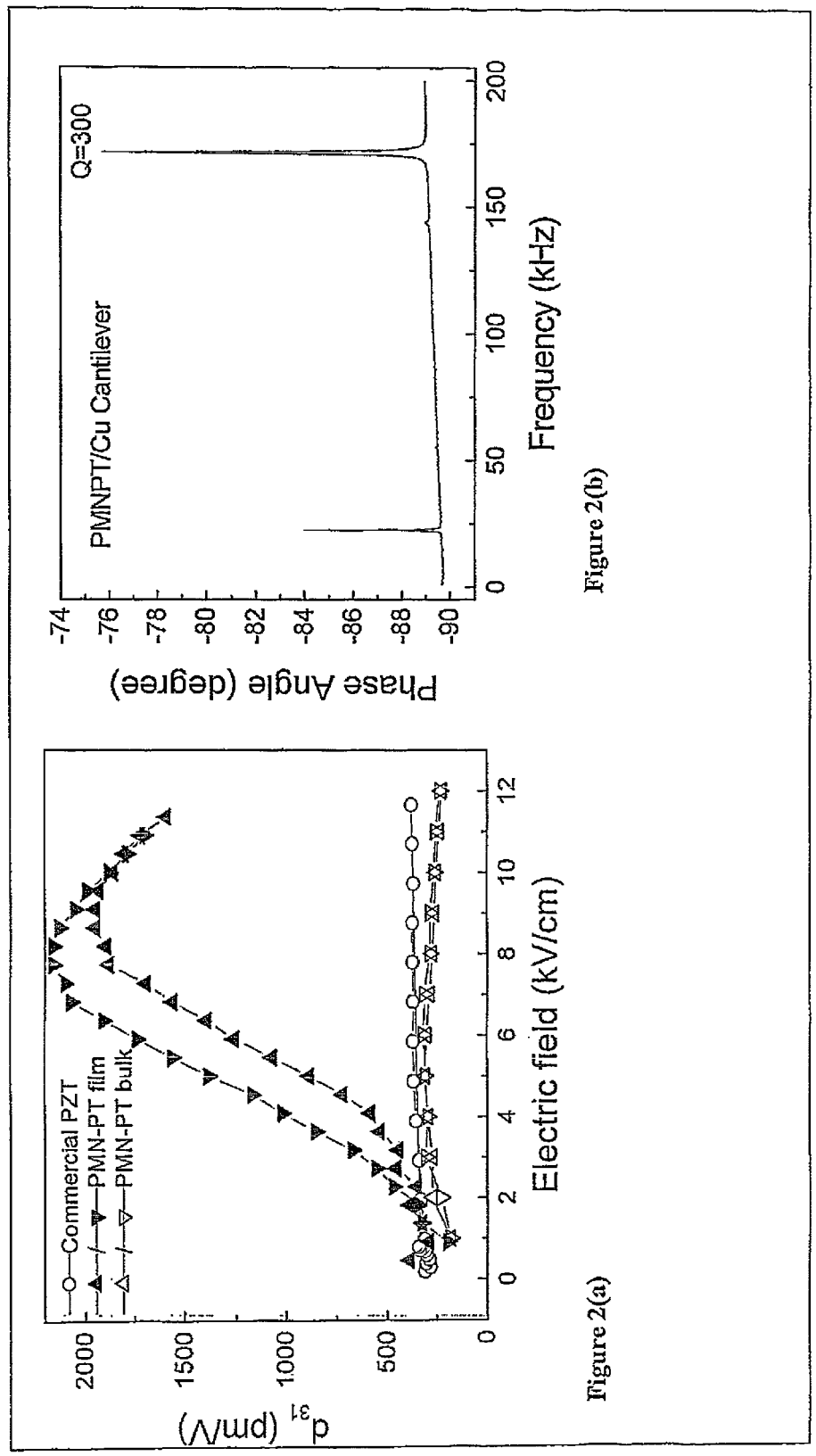
FIG. 2(a) is a graph of piezoelectric coefficient, $-d_{31}$, versus electric field for PMN microcantilevers in accordance with the present invention.
FIG. 2(b) is the resonance spectrum of a PMN—PT PEMS

Further, PMN—PT freestanding films with thicknesses of 8 μm or 22 μm were found to exhibit an extremely high electric-field enhanced piezoelectric $-d_{31}$ coefficient of 2000 μm/V at E=10 kV/cm, as shown in FIG. 2(a), which is about 7 times that of the bulk PMN—PT and commercial PZT, and which also exceeds the piezoelectric coefficient of specially-cut single crystalline PMN—PT. The direction of the triangles in FIG. 2(a) indicate whether the results were obtained when the field was ramped up or down. The piezoelectric coefficient $-d_{31}$ is calculated according to (Equation 1), $$d_{31} = \frac{h_{can}}{3VL^2} \cdot \frac{E_1^2 t_1^4 + E_2^2 t_2^4 + 2E_1 t_1 E_2 t_2 (2t_1^2 + 2t_2^2 + 3t_1 t_2)}{E_1 E_2 t_1 (t_1 + t_2)(1 - v)}, \quad \text{(Equation 1)}$$

where V is the applied voltage, L, the cantilever length, v the Poisson ratio, $E_1$, and $E_2$ ($t_1$ and $t_2$) are the Young's modulus (thickness) of copper and that of PMN—PT, respectively. The large piezoelectric coefficient $-d_{31}$ is believed to be due to (1) low-temperature sinterable PMN—PT powder that enables the film to sinter below 1000° C. to avoid lead loss and maintain the correct stoichiometry, and (2) freestanding film geometry that aligns the polarization in the plane of the film. Polarization reorientation by the applied electric field, normal to the film, enhances the piezoelectric coefficient. By using sinterable PMN powders and eliminating defects through careful placement of the thin films on a substrate, the PMN—PT films were endowed with superior piezoelectric properties. This fabrication method is robust and may be readily applied to other lead based piezoelectrics and non-lead-based materials.

In another embodiment a PEMS may be constructed from highly piezoelectric lead zirconate titanate (PZT). (PZT)/$SiO_2$ PEMS may be configured to form microcantilevers less than 20 μm long having attogram sensitivity of $10^{-18}$ g/Hz, a piezoelectric layer thickness of about 1.0-μm-8 μm, more preferably, less than about 4 μm, about 1.5-μm-2 μm or less than about 2 μm and a dielectric constant of at least 1600, more preferably, at least 1900. The PZT PEMS is capable of exhibiting up to four resonance peaks with quality values, Q, ranging from a minimum of about 20 to between 120 and 320. (PZT)/$SiO_2$ PEMS may also be configured to have a thickness of less than 2 μm and a length of less than 30 μm. The dielectric constants can be further raised to above 2000 and up to about 3000 by any standard method of doping the piezoelectric layer.

Figure 3:
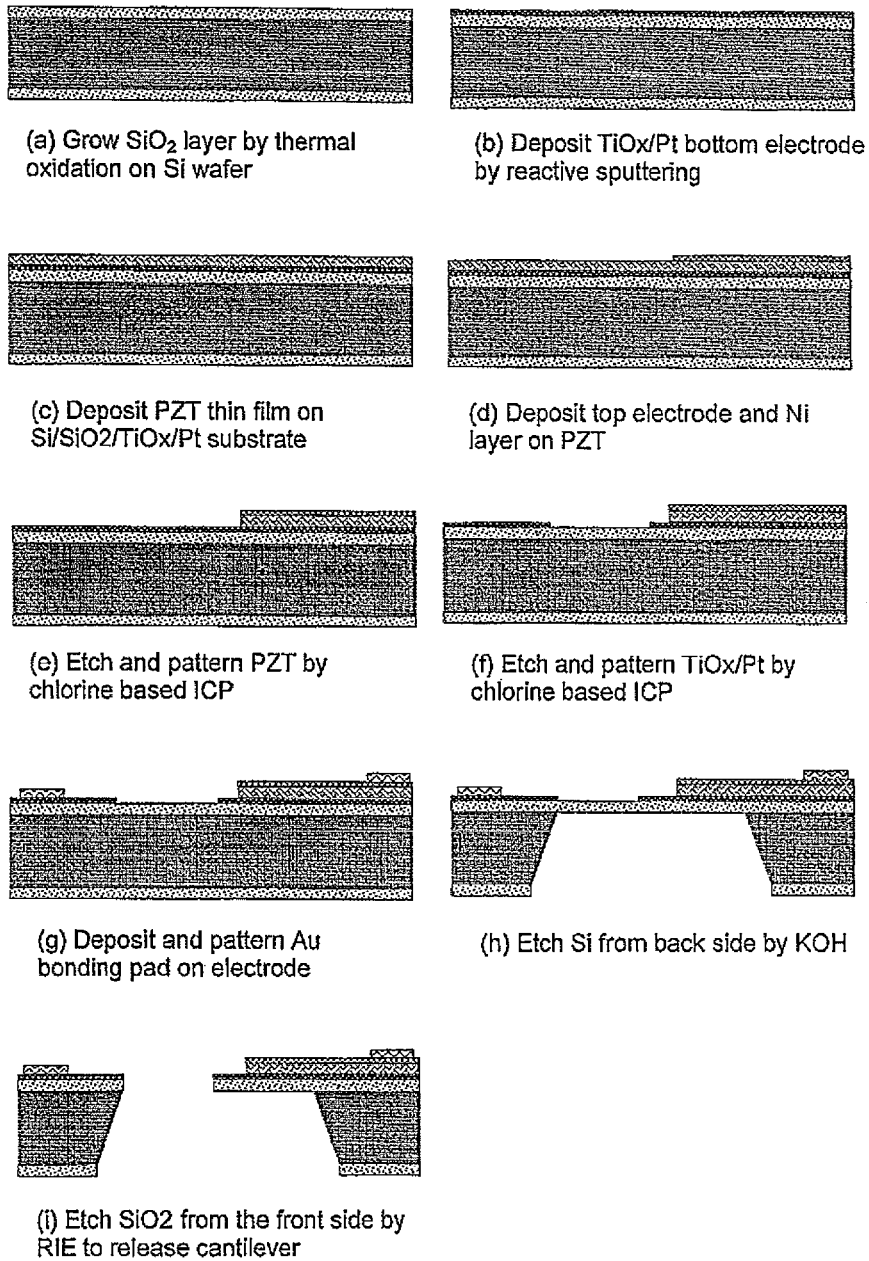
FIG. 3 is a schematic showing a preferred micro-fabrication procedure for constructing PZT/SiO$_2$ microcantilevers in accordance with the present invention.

A PZT/$SiO_2$ piezoelectric layer 7 of film may be formed on silicon wafers and attached to a substrate, such as glass, to form an array. It is also possible to fabricate thin PZT films, of 1.0 to 2.0 μm in thickness, on a variety of different substrates using a sol-gel process. FIG. 3 depicts a preferred microfabrication procedure for constructing PZT/SiO$_2$ piezoelectric microcantilever sensors.

One advantage of this invention is the ability to construct a microcantilever from one piece of PZT/SiO$_2$ film without having to separately attach the non-piezoelectric 6 and piezoelectric layers 7. Because the cantilevers thus fabricated have clean interfaces between the PZT/SiO$_2$ layer and the electrodes, the cantilevers exhibit high Q values. The resultant clean geometry of the microcantilever increases sensitivity and facilitates the manufacturing process.

The self-actuating and self-detecting PEMS of the present invention overcomes a significant problem of the prior art, miniaturizing microcantilevers without losing high resonance-peaks. In the present invention, the novel PMN and PZT micro-fabrication methods produce thin piezoelectric PEMS having enhanced sensitivity, as evidenced by the large dielectric constants, piezoelectric coefficients and Q values.

Figure 4A:
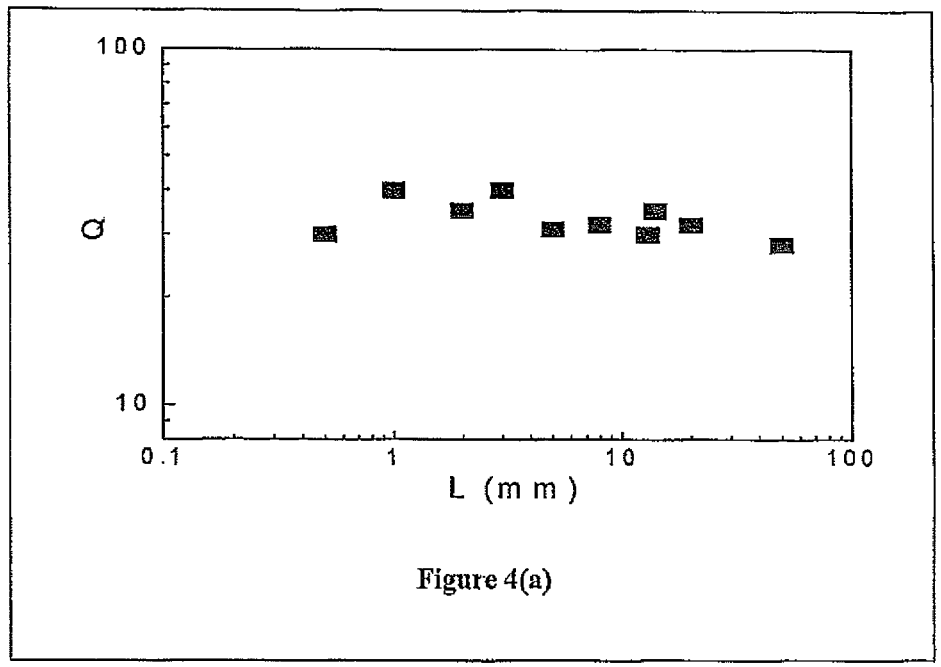
FIG. 4(a) is a graph of quality value (Q) versus cantilever length for PZT cantilevers in accordance with the present invention.
Figure 4B:
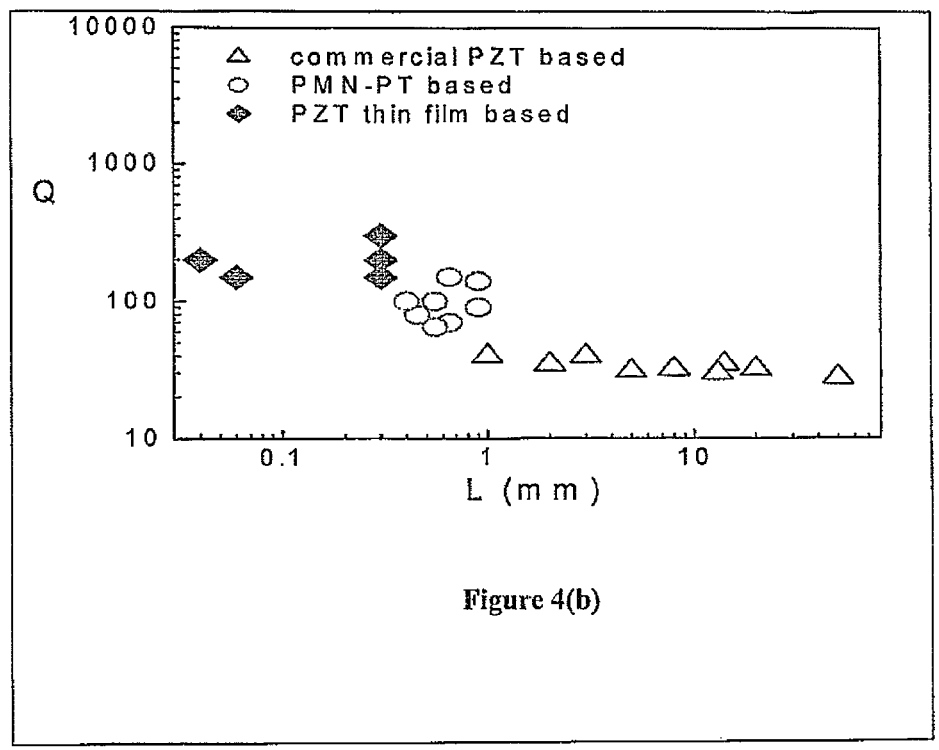
FIG. 4(b) is a graph of quality value (Q) versus cantilever length for PZT and PMN—PT PEMS in accordance with the present invention.

Q values are an excellent indicator of cantilever sensitivity. Although it is expected that the Q value of silicon microcantilevers decreases with cantilever size, FIG. 4 shows that the Q value of a commercial-PZT-based piezoelectric microcantilever remains approximately the same even though the microcantilever length varies over two orders of magnitude due to the polycrystalline composition of the piezoelectric layer 7. The piezoelectric layer 7 of the present invention therefore utilizes polycrystalline compositions such as PMN—PT and PZT in order to miniaturize PEMS without losing sensitivity. For example, by reducing PZT PEMS to a length-scale of 300 µm and 50 PMN—PT and PZT PEMS are capable of attaining detection sensitivity greater than $10^{-15}$ and $10^{-18}$ g/Hz, respectively. Freestanding PMN—PT PEMS 500-700 µm in length are capable of achieving Q values higher than 300. Additionally, PEMS with a thickness of less than 5 µm and length of less 120 µm long, may achieve a sensitivity better than $10^{-16}$ g/Hz.

To further increase sensitivity and expedite the detection process, the PEMS may be immersed in a flowing solution for in-solution detection. The PEMS is preferably situated in a flow cell system to enable tailored, rapid and simultaneous detection and quantification of multiple organic compounds or molecules.

Figure 5A:
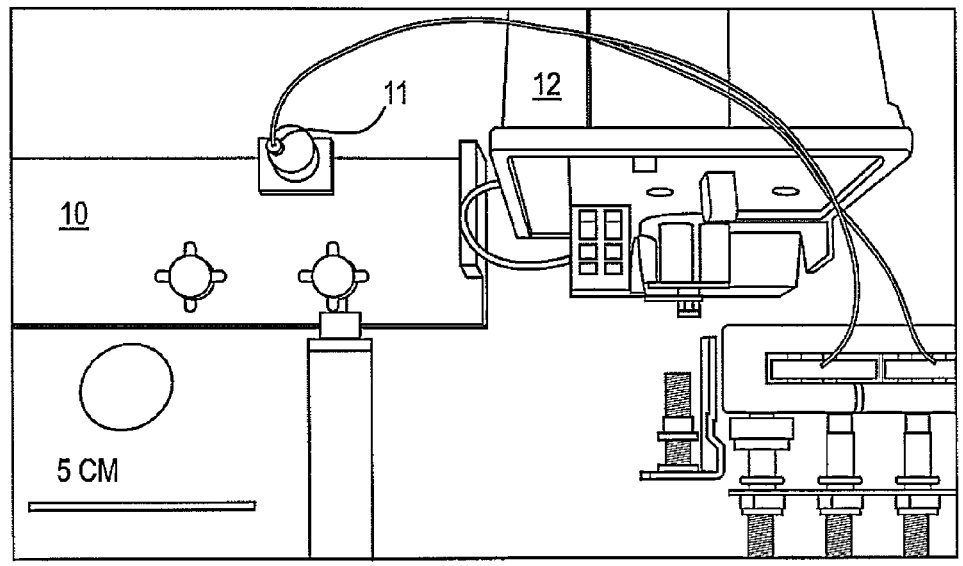
FIG. 5(a) depicts a flow cell system which can be used in conjunction with the cantilevers of the present invention.
Figure 5B:
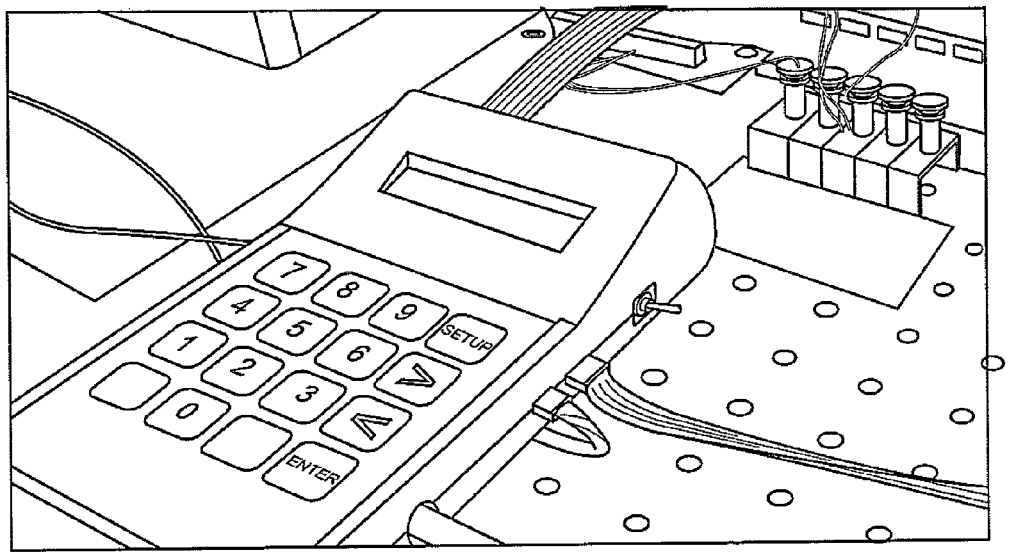
FIG. 5(b) depicts a 3.5 in by 7.5 in portable PEMS sensor capable of working with 8 sensors and powered by a 9-V battery.

FIG. 5(a) shows a flow cell system 10, with a PEMS holder/measuring unit 11, having a total volume of less than 0.03 ml, pump 12, and a mechanism for controlling temperature and humidity (not shown). The flow cell 10 may attain flow rates of up to 1 ml/min. The total volume of the flow cell, number of channels and flow rate may vary depending upon the number of compounds to be measured. The flow cell 10 may cooperate with a portable PEMS unit, shown in FIG. 5(b), which has multiple channels for the simultaneous quantification of multiple receptor specific molecules. The portable PEMS is inexpensive and capable of obtaining quick measurements.

Another means for further enhancing sensitivity is by increasing humidity. The mass change per unit area per percent humidity change of PZT PEMS is estimated to be about $1.2 \times 10^{-11}$ g/Hz/mm$^2$/% humidity. The sensitivity of PMN PEMS by comparison is known to be about three times greater than that of PZT PEMS.

The resultant PEMS are chemically inert, thermally stable and miniaturized to enhance sensitivity. They function by binding target molecules that react to the receptors immobilized on the electrodes. The corresponding change in mass shifts the mechanical resonance frequency of the microcantilever. The PEMS is capable of detecting these shifts in resonance frequency by monitoring the $i^{th}$-mode flexural resonance frequency $f_i$, which is related to the effective spring constant, $K_e$, and effective mass, $M_e$, of the piezoelectric cantilever at the tip as shown in Equation 2.

$$f_i = \frac{1}{2\pi}\sqrt{K_e/M_e} \quad \text{(Equation 2)}$$

Figure 6:
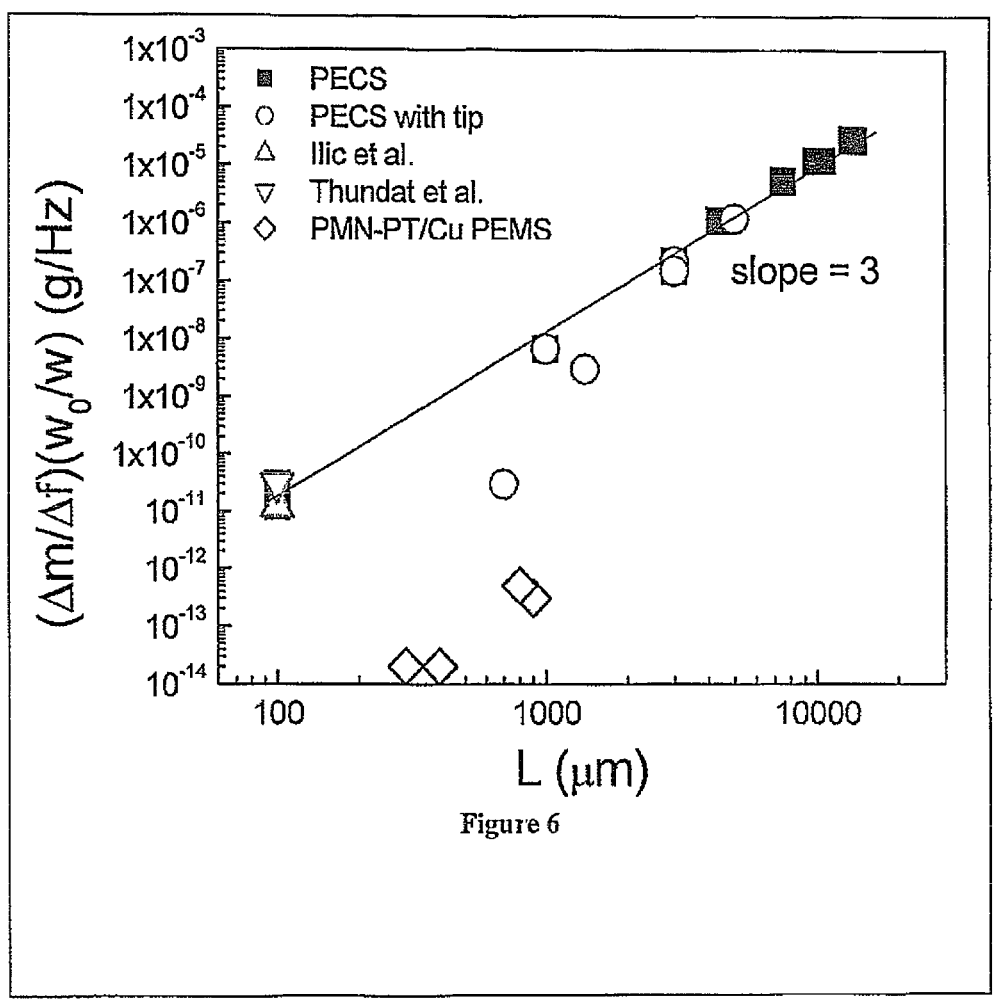
FIG. 6 is a graph of Δm/Δf as a function of cantilever length.
Figure 7:
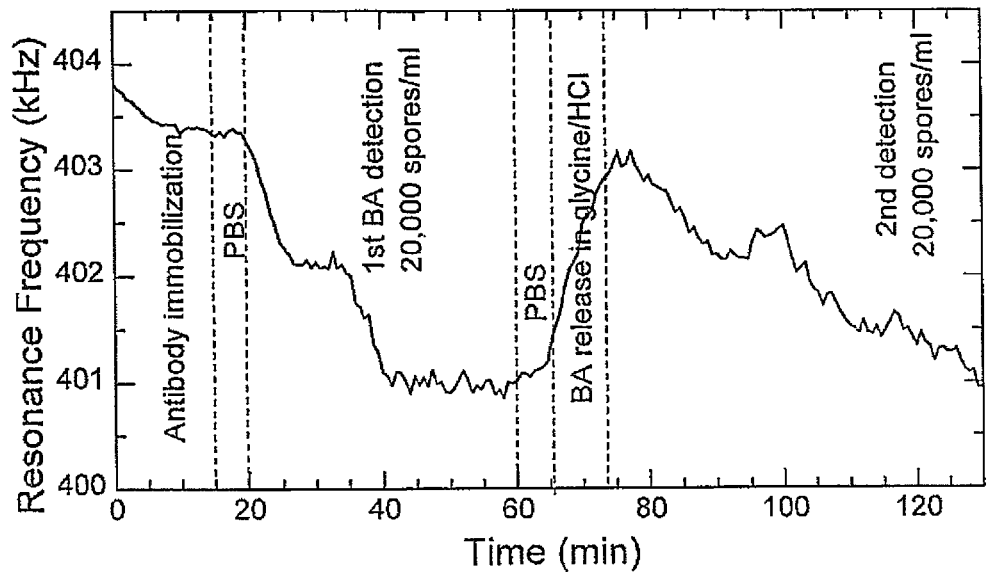
FIG. 7 is a graph of resonance frequency shift as a function of time for the microcantilever PEMS-B.
Figure 8:
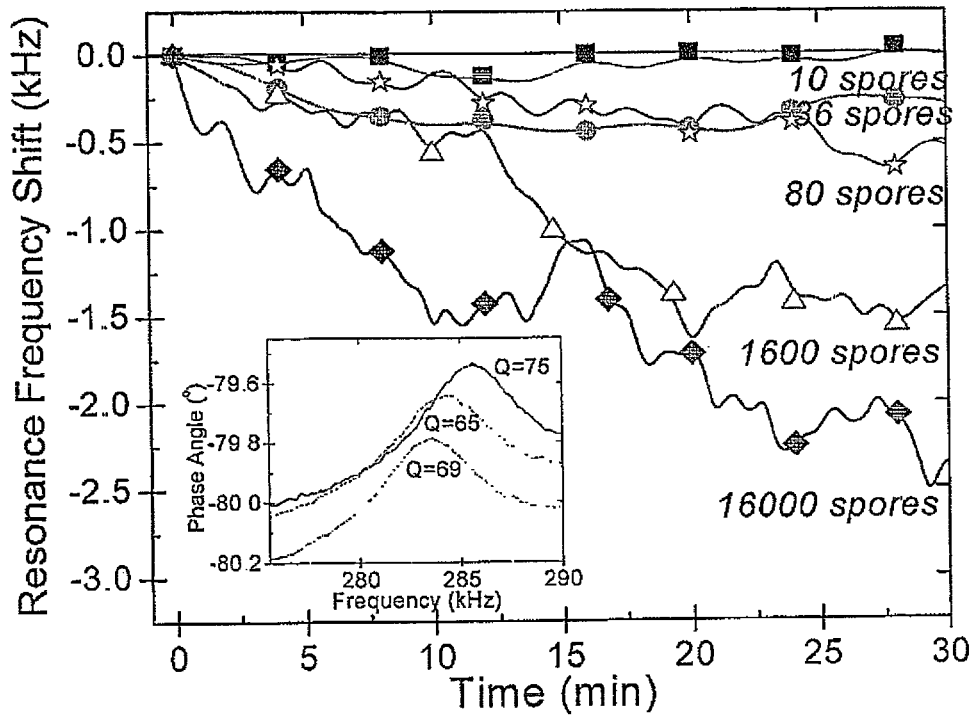
FIG. 8 is a graph of resonance frequency shift as a function of time for the microcantilever PEMS-B using a resonance peak of 285 kHz.

The binding of a receptor specific molecule to the cantilever surface changes the cantilever mass and the cantilever spring constant. The resonance frequency shift Δf, expressed in Equation 3, $$\Delta f_i = f_i\left(-\frac{\Delta m}{2M_e} + \frac{\Delta k}{2K_e}\right), \quad \text{(Equation 3)}$$

where Δm and Δk denote the mass change and the effective spring constant, model the functionality of the microcantilever. FIG. 6 shows the Δm/Δf of PMN—PT/Cu PEMS constructed from 8 µm and 22 µm thick PMN—PT films. The full circles and full squares of FIG. 6 represent results obtained with millimeter long PEMS, with and without a stainless steel tip, respectively. The Δm/Δf of these PEMS deviates from the solid line by more than three orders of magnitude, thereby indicating that reducing the PEMS thickness and dimension binding-related stress greatly enhances the resonance frequency shift.

These PEMS may be used for various sensing applications such as solid-liquid transition detectors, liquid viscosity and density sensors, mass sensors for in situ and in-water detection. PEMS may generally be used for detection of any molecule or organic compound.

The PEMS technology may be particularly promising for the detection of bioterrorism agents. Antibody receptors specific to at least one bioterrorism agent may be bound to an electrode and used to detect the presence of a bioterrorism antigen. In addition to identifying the existence of a bioterrorism agent, it may also be used to quantify the concentration of the agent.

Additionally, PEMS may be useful in the health sciences as a diagnostic instrument. It may be used as a means for early detection of cancers and other diseases. It may also be used to monitor the progress of the disease throughout treatment. The PEMS may be incorporated in a portable device and used as a noninvasive means for testing blood and other bodily fluids for various pathogens, infectious agents and other markers indicative of disease.

PEMS may also be particularly applicable for the food science and food manufacturing industry. PEMS may be used as a diagnostic instrument for detecting pathogens or other disease agents present in food supplies and prepared or processed foods. Additionally, it may also be useful in manufacturing plants and food service industries as a means of intermittently checking food products during different phases of food preparations thereby preventing contamination and the spread of bacterial or viral diseases such as *salmonella* and *E. coli*.

EXAMPLES

Example 1

PMN—PT/Sn PEMS were used in-situ to detect the presence of *Bacillus anthracis* (BA), a bioterrorism agent. Two PEMS, PEMS-A (500 μm long, 800 μm wide, with a 22 μm thick PMN—PT layer, a 20 μm thick tin layer and a $1 \times 10^{-12}$ g/Hz mass detection sensitivity) and PEMS-B (350 μm long, 800 μm wide, with an 8 μm thick PMN—PT layer, a 6 μm thick tin layer and a $3 \times 10^{-13}$ g/Hz mass detection sensitivity) were inserted in a flow cell through which a solution containing BA was pumped.

Figure 9:
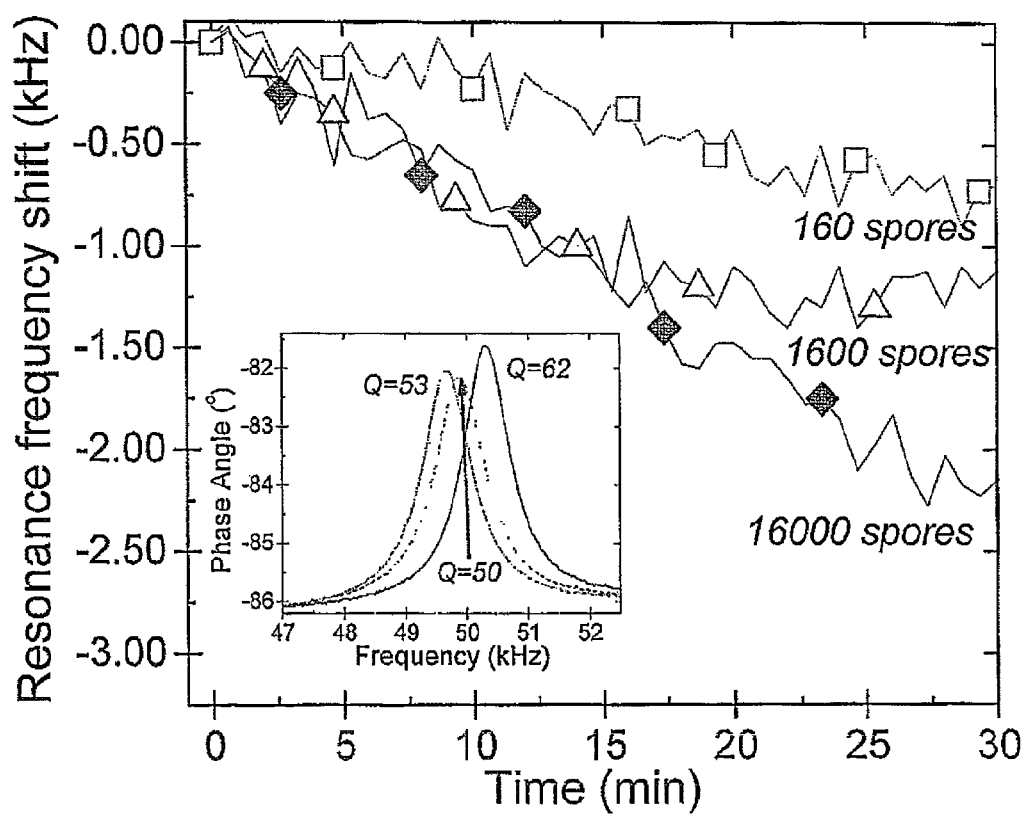
FIG. 9 is a graph of resonance frequency shift as a function of time for the microcantilever PEMS-A.
Figure 10:
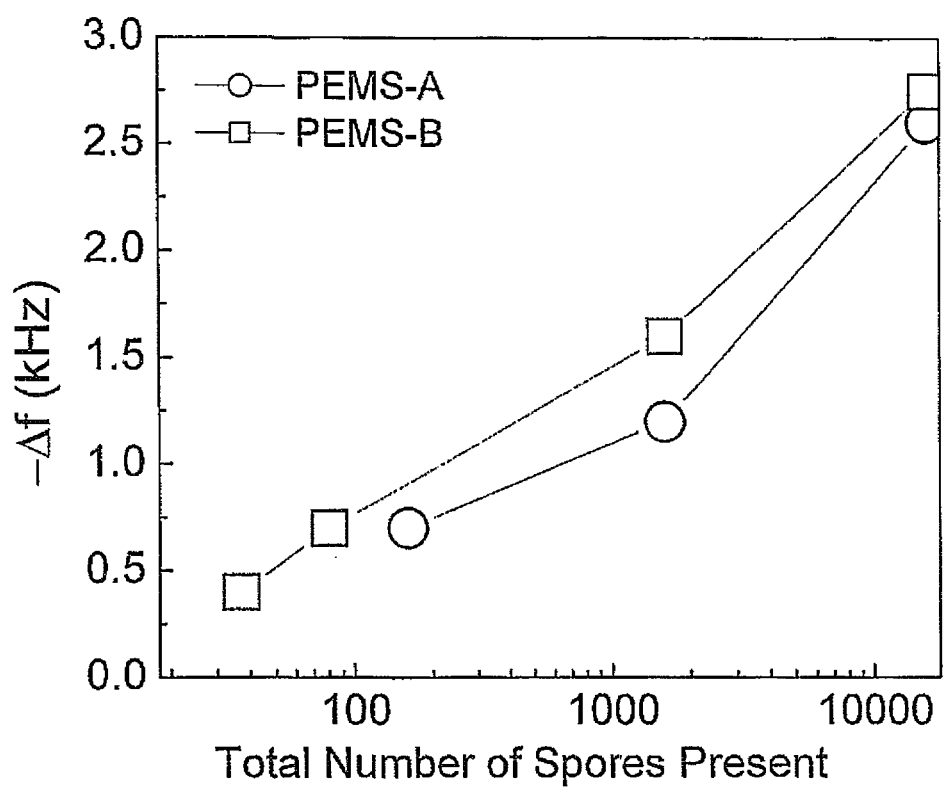
FIG. 10 is a graph of resonance frequency shift as a function of the total number of BA spores for both microcantilevers PEMS-A and PEMS-B.

The experiment demonstrates that in phosphate buffered saline (PBS) solution, the PEMS were capable of achieving Q values ranging from 50 to 75. PEMS-A exhibited resonance frequency shifts of 2100±200, 1100±100 and 700±100 Hz at concentrations of 20000, 2000, and 200 spores/ml or 16000, 1600, and 160 total spores, respectively. PEMS-B exhibited resonance frequency shifts of 2400±200, 1500±200, 500±150 and 200±100 Hz at concentrations of 20000, 2000, 100, and 45 spores/ml or 16000, 1600, 80, and 36 total spores, respectively.

The PEMS were fabricated from PMN—PT freestanding films 22 μm and 8 μm in thickness and electrically insulated with methyltrimethoxysilane (MTMS) coatings on the tin surface. A 30 nm thick nickel layer with a 15-30 nm thick chromium bonding layer was first deposited on one side of the PMN—PT freestanding film by evaporation using an E-gun evaporator as the electrode. A tin non-piezoelectric layer was then electroplated on the nickel surface at a rate of 0.5 μm/minute, using tin sulfate in a plating solution. A 150 nm thick platinum on a 10-nm thick titanium layer was evaporated on the other face of the film as the other electrode. The resultant PMN—PT/Sn bilayer was embedded in wax and cut into the cantilever shape with a wire saw. Gold wires were attached to the top and bottom electrodes using conductive glue for electrical connection. The PMN—PT/Sn strips were finally glued to a glass slide or a plastic substrate with epoxy to form the microcantilever geometry.

To insulate the tin electrode of these PMN—PT/Sn PEMS, the PEMS were first soaked in a diluted (1:40 in water) piranha solution (one part of 98% sulfuric acid with one part of 30% hydrogen peroxide) at 20° C. for 2 mM. Methyltrimethoxysilane (MTMS) was then spin coated on the tin surface at 2000 rpm and cross linked (pH=9.5 for 2 hr) twice to form two MTMS coatings on the tin surface.

For antibody immobilization, the platinum electrode was cleaned with a 1:40 diluted piranha solution for 2 min followed by soaking the PEMS in a 2 mM 3-mercaptopropionic acid (MPA) for 2 hr to form an MPA monolayer on the Pt surface. The carboxyl group of the MPA was then activated by a solution of 2 mM N-Ethyl-N'-(3-dimethylaminopropyl)carbodiimide (EDC) and 5 mM N-hydroxysuccinimide (NHS) in water to allow covalent bonding of primary amines on the anti-BA-spore antibody to the MPA on the platinum surface.

Anti-BA IgG antibodies were then immobilized on the platinum electrode of the PMN-PT layer by first mounting the insulated PEMS with activated MPA in a specifically designed holder and vertically inserting the PEMS into the center of a custom polycarbonate flow cell, 1 mm wide by 1 mm high by 10 mm long with its major faces parallel to the flow and capable of holding a liquid volume of 0.8 ml. A baseline of pure phosphate buffered saline (PBS) solution was run through the flow cell for several minutes before injecting a 600 nM antibody solution into the flow cell for 40 min, after which the flow system was once again rinsed with pure PBS. The flow rate used for antibody immobilization and subsequent BA binding was 1 ml/min, which corresponded to a Reynolds number of 1.6 and a flow speed of 2.5 cm/s over the PEMS surface.

Subsequently, 0.8 ml of the desired concentration of ultraviolet (UV)-killed, Sterne strain 7702 BA spores were injected into the flow system and run for 30 minutes. BA spores were then release from the sensor surface in a mixture of glycine and HCl at pH of 2.5 for 7 min. The total volume of the liquid utilized was only 0.8 ml; thus, the actual number of spores available for detection by the cantilever is actually only 80% of the indicated concentration. Scanning electron microscopy (SEM) was performed to confirm spore detection and sensitivity calculations.

FIG. 7 shows the time evolution of a 404 kHz resonance frequency of PEMS-B during antibody immobilization, BA spore detection, and spore release. The antibody solution was introduced at t=0. The resonance frequency shift during t=0-15 mM corresponds to the immobilization of the antibody to the PEMS platinum surface. The resonance frequency decreased 0.4 kHz from 403.8 kHz at t=0 min to 403.4 kHz at t=15 min due to the binding of the antibody to the MPA on the platinum surface. This resonance frequency shift saturated at t=10 min and Δf=−0.4 kHz, indicating the immobilization took about 10 min, approximately the same as dipping in static solution. At t=15-20 min the antibody solution was replaced with PBS. As can be seen, there was no significant shift in that period. At t=20 min, when 0.8 ml of a 20,000 spores/ml (16,000 total spores) BA suspension was introduced into the flow cell, the resonance frequency rapidly decreased from 403.4 kHz at t=20 min to 401 kHz at t=40 min with a Δf=−2.4 kHz. This resonance frequency shift during t=20-40 min corresponded to the binding of spores to the antibody immobilized on the PEMS surface. At t=60-65 min, the spore suspension was replaced by PBS, again resulting in no significant resonance frequency shift in that period. From t=65-72 min, the release of the bound spores from the sensor surface in glycine/HCl solution was performed resulting in a recovery (up-shift) to 403.1 kHz at t=72 min, nearly the value before the detection. The second detection period with 0.8 ml of a suspension of 20,000 spores/ml (16,000 total spores) was started at t=72 min. As can be seen, the second detection at the same concentration exhibited a resonance frequency shift similar to the first detection. FIG. 7 therefore shows that the PEMS may be completely submerged in PBS while detecting the binding of proteins and spores to the sensor surface by monitoring the resonance frequency down-shift of a particular peak. Conversely the release of the antigen can be detected by monitoring the resonance frequency up-shift as is shown during the release of the spores by glycine/HCl solution.

FIG. 8 shows the plot of a resonance frequency shift of PEMS-B versus time using a resonance peak of 285 kHz at BA spore concentrations of 20,000 spores/ml (16,000 total spores), 2000 spores/ml (1600 total spores), 100 spores/ml (80 total spores), 45 spores/ml (36 total spores) and 12 spores/ml (10 total spores). Also shown inset in FIG. 8 are several in-PBS resonance spectra of PEMS-B during the BA spores detection at the 20,000 spores/ml concentration. The solid line, the dashed line, and the dashed-dotted line represent the resonance spectrum at t=0, 15 and 30 min, with Q values of 75, 65 and 69 respectively (where Q is ratio of the resonance frequency to the resonance peak width at half of the peak height). As can be seen in FIG. 8, resonant frequency shifts of 2400±200, 1500±200, 500±160, and 200±100 Hz were observed at t=30 min for 16000, 1600, 80, and 36 total spores, respectively. As the concentration was reduced to 12 spores/ml (10 total spores), no discernable resonance frequency shift could be resolved from the sensor noise.

FIG. 9 shows a plot of the resonance frequency shift of PEMS-A versus time for concentrations of 20,000 spores/ml (16,000 total spores), 2,000 spores/ml (1,600 total spores) and 200 spores/ml (160 total spores). The insert in FIG. 9 shows the in-PBS resonance spectra of PEMS-A at t=0, 15, and 30 min with Q=62, 50, 53 as the solid, dashed, and dashed-dotted lines, respectively during the detection of BA spores at 16000 total spores. As is shown in FIG. 9, at t=30 min these concentrations yielded frequency shifts of 2100±200, 1100±100, and 700±100 Hz, respectively. FIG. 4 also reveals that, for the lower spore levels of 160 and 1,600, the resonance frequency shift begins to level off at approximately 20 minutes while for the higher spore level of 16,000, the resonance frequency continues to decrease during the entire detection period as similar to the situations with PEMS-B. The resonance frequency shifts versus total number of BA spores of both PEMS-A and PEMS-B are summarized in FIG. 10.

The experimentally obtained mass detection sensitivities are more than 100 times more sensitive than the theoretical mass sensitivity values suggested by considering simply the mass loading effect alone.

Example 2

A PZT/SiO$_2$ piezoelectric cantilever sensor (PECS) 0.5 mm long and 2 mm wide, 5 MHz QCM and various PMN—PT PEMS were tested for in-situ detection of prostate specific antigen (PSA). The tip of each cantilever were partially immersed in PSA solutions of 26.1, 17.5, 8.76, 4.38, and 2.19 µg/ml to a depth of approximately 1 mm for approximately 30 minutes. The tip was immersed in a vertical orientation in order to ensure that there was no nonspecific binding due to gravity. Between detections, the antibody surface of each cantilever was regenerated by a brief dip in HCl-glycine solution.

Figure 11A:
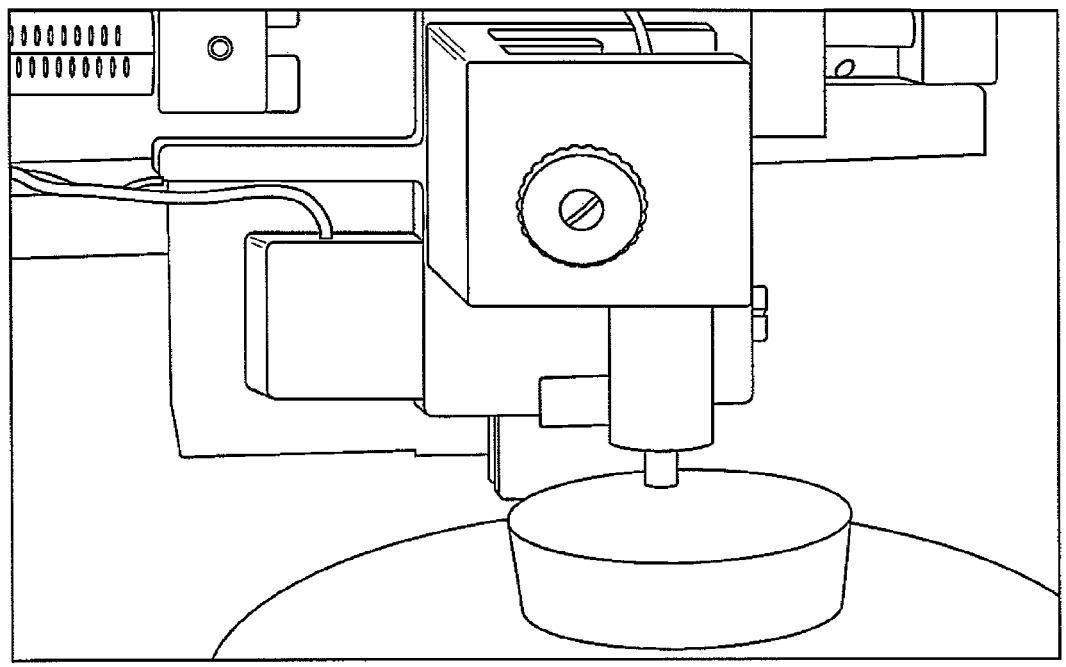
FIG. 11(a) depicts an experimental setup for determining the resonance frequency shift for a 1 mm long PZT/glass cantilever having a 2 mm long glass tip.
Figure 11B:
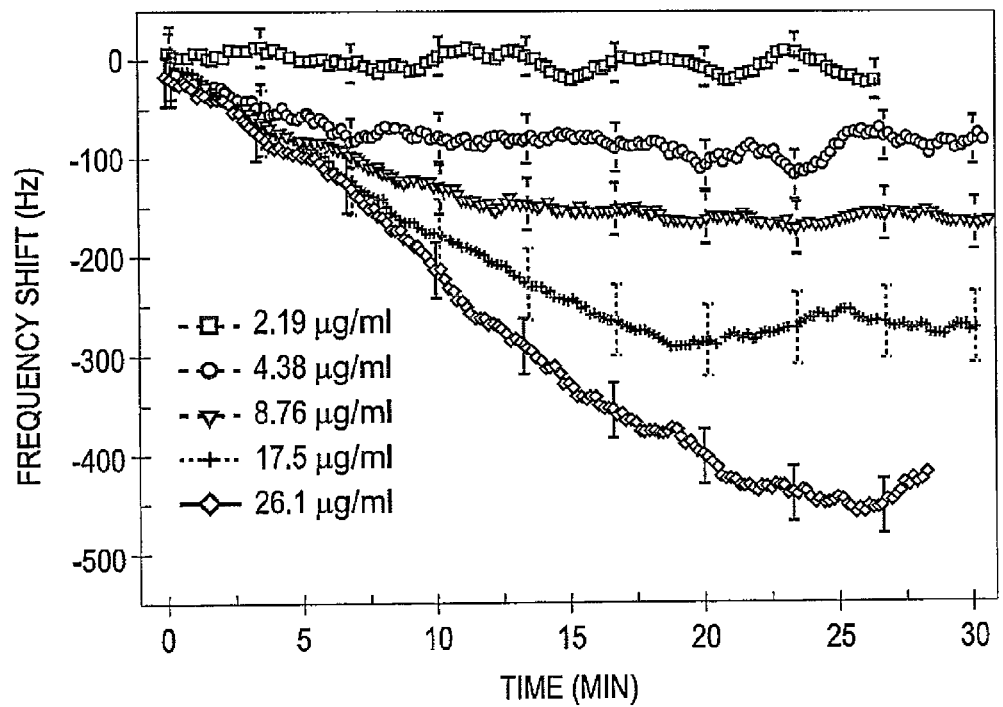
FIG. 11(b) is a graph of resonance frequency shift as a function of time of the PEMS of FIG. 11(a).

The QCM sensor exhibited a resonance frequency shift of 45 Hz for antibody immobilization; PECS exhibited a resonance frequency shift of 450 Hz. Using the QCM resonance frequency value and the Sauerbrey equation, the mass change per unit area due to the antibody immobilization was determined to be $3.5 \times 10^{-9}$ g/mm. In comparison, the detection sensitivity for a piezoelectric cantilever sensor, shown in FIG. 11(a), was determined to be approximately $3 \times 10^{-11}$ g/Hz. FIG. 11(b) and Table 2 shows the detection curves for the piezoelectric cantilever and demonstrates that the cantilever is only capable of detecting PSA at 4 µg/ml and above.

Figure 12:
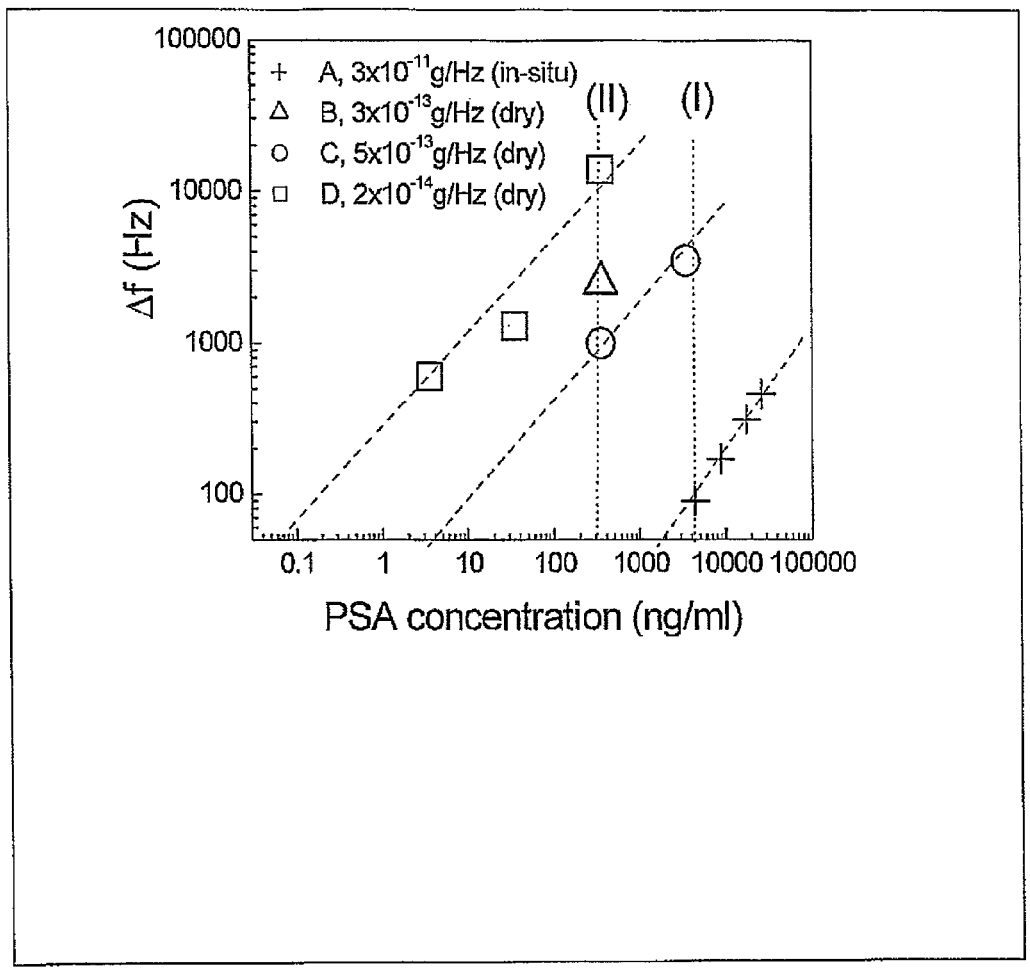
FIG. 12 is a graph of frequency shift as a function of PSA concentration for various cantilevers

PMN—PT microcantilever, represented by circle data points in FIG. 12, was found to have a sensitivity of $5 \times 10^{-13}$ g/Hz. Based on these sensitivities, it is possible to easily detect PSA at 3.5 ng/ml with a resonance frequency over 500 Hz. Also plotted in FIG. 12 are the in situ resonance frequency shifts obtained from the PZT/glass cantilever, which are represented by the cross shaped data points. The intercept of the dashed lines with the 50 Hz base line suggests the concentration limit of these microcantilevers. For the in situ results of FIG. 12, the intercept was determined to be the detection limit of the PZT/glass cantilever.

In situ detection is therefore predicted to have background resonance frequency uncertainties of no more than 50 Hz. Using 50 Hz as a cutoff at the base line of FIG. 12, the extrapolated detection limit was 0.1 ng/ml for microcantilever D with $2 \times 10^{-14}$ g/Hz sensitivity, which was already as good as or better than the sensitivities of commercial PSA testing techniques while the present in situ measurements have the advantages of rapid detection and low cost.

Example 3

There exist a number of means for immobilizing various receptors on various different electrode surfaces. The immobilization methods may differ depending upon the receptor to be bound on the electrode surface.

For example, BA antigens may be immobilized on a lead surface by cleaning a platinum electrode with a 1:40 diluted piranha solution for 2 min, soaking the PEMS in a 2 mM 3-mercaptopropionic acid (MPA) for 2 hr to form an MPA monolayer on the electrode surface, and activating the carboxyl group of the MPA using a solution of 2 mM N-Ethyl-N'-(3-dimethylaminopropyl)carbodiimide (EDC) and 5 mM N-hydroxysuccinimide (NHS) in water to allow covalent bonding of primary amines on the anti-BA-spore antibody to the MPA monolayer.

A method for PSA receptor immobilization on a lead surface includes the steps of immersing the microcantilever in a solution containing 1 part 30% $H_2O_2$, concentrated $H_2SO_4$ and 29 parts water for 2 min, rinsing with distilled water and immersing in a 1 mM MPA aqueous solution overnight. The

TABLE 2

Frequency shift at 20 minutes

| Detector Type | Detection sensitivity | Label-free | Direct, In-situ | Rapid | High-throughput | Multiplexing |
|---|---|---|---|---|---|---|
| PEMS | $10^{-15}$-$10^{-18}$ g | yes | yes | yes | yes | yes |
| QCM | $10^{-9}$ g | yes | yes | Yes | No | no |
| Silicon microcantilever | $10^{-12}$ g | yes | no | No | No | no |
| Optical fiber fluorescence | | no | no | No | Yes | yes |
| ELISA[26] | $10^{-10}$ g | no | no | No | Yes | yes |
| SPR[3] | $10^{-12}$ g | yes | yes | Yes | No | no |

By comparison, the sensitivities of various PMN PEMS were determined by subjecting the PEMS to a controlled 70% humidity and 16° C. environment in which they were immersed in a flowing PSA solution of various concentrations. FIG. 12 shows that a 340 µm long, 750 µm wide and 8 µm thick PMN—PT/Cu microcantilever, represented in FIG. 12 by square data points, was found to have a sensitivity of $2 \times 10^{-14}$ g/Hz; a 900 µm long, 750 µm wide and 8 µm thick PMN—PT/Cu microcantilever, represented by triangle data points in FIG. 12, was found to have a sensitivity $3 \times 10^{-13}$ g/Hz; and an 800 µm long, 750 µm wide and 22 µm thick microcantilever tip is then rinsed with distilled water and activated by immersing in a solution containing 5 mg/ml 1-ethyl-3-(3-dimethylaminopropy)carbodimide hydrochloride (EDC), 5 mg/ml N-hydroxysulfosuccinimide (NHS) and distilled water for 30 min. 1 µl of a 0.1 mg/ml solution containing anti-PSA in PBS at a pH of 7.4 was then coated on the cantilever surface for 30 min.

scFv receptors may be immobilized on a gold surface by binding activated MPA to the amine of lysine in the scFv. The immobilization method includes the steps of coating MPA on the gold-coated cantilever tip, activating the MPA with a solution of 5 mg/ml 1-ethyl-3-(3-dimethylaminopropy)carbodiimide hydrochloride (EDC), 5 mg/ml N-hydroxysulfosuccinimide (NHS) and distilled water for 30 min and partially immersing the microcantilever in the scFv solution. Alternatively, it may be possible to utilize longer mercaptoundecanoic acid (MUA) in order to optimize the efficiency.

scFv receptors may also be immobilized on a gold surface by using $Cu^{2+}$ ions to bind to His6 tag of scFv. In this method, the gold coated microcantilever tip is first cleaned with Piranha solution for 10 minutes and rinsed with distilled water. The gold surface is then treated with MPTS, MPA (mercaptopropionic acid), or MUA (mercaptoundecanoic acid) to form a monolayer on the gold-coated sensor surface. Preferably, the gold surface is treated by immersed in a solution of 1 mM 11 Mercaptoundecanoic Acid (MUA) and ethanol for 3 hours and rinsed with distilled water. The cantilever is then immersed in a 2 mM $Cu(ClO_4)_2$ aqueous solution for 10 min to adsorb $Cu^{2+}$ on the MUA self assembled monolayer and form a MPA-Cu composite monolayer. A monolayer of Cu ions will bind to the His6 tag at the C-terminal of scFv. The cantilever may then be partially immersed in the scFv solution for in-situ monitoring the binding of the scFv to the $Cu^{2+}$ ions on the cantilever tip surface.

Another immobilization method of scFv to a $SiO_2$ surface entails cleaning an electrode surface using strong acid, reacting the surface with Glycidoxypropyl trimethoxysilane (GOPTS) to generate epoxy groups. The surface is then reacted with amine groups of lysine in scFv. Alternatively, it may be possible to utilize other bifunctional linkers such as alkoxysilane-PEG-carboxyl on the $SiO_2$ surface. The surface is then treated with $Cu(ClO_4)_2 \sim 6H_2O$ or $CuCl_2$ to create $Cu^{2+}$ ions on the surface that to bind the His6 tag or cysteine tag at the c-terminal of the scFv. The length of the PEG may vary to obtain optimal antigen-receptor binding.

Example 4

Figure 13A:
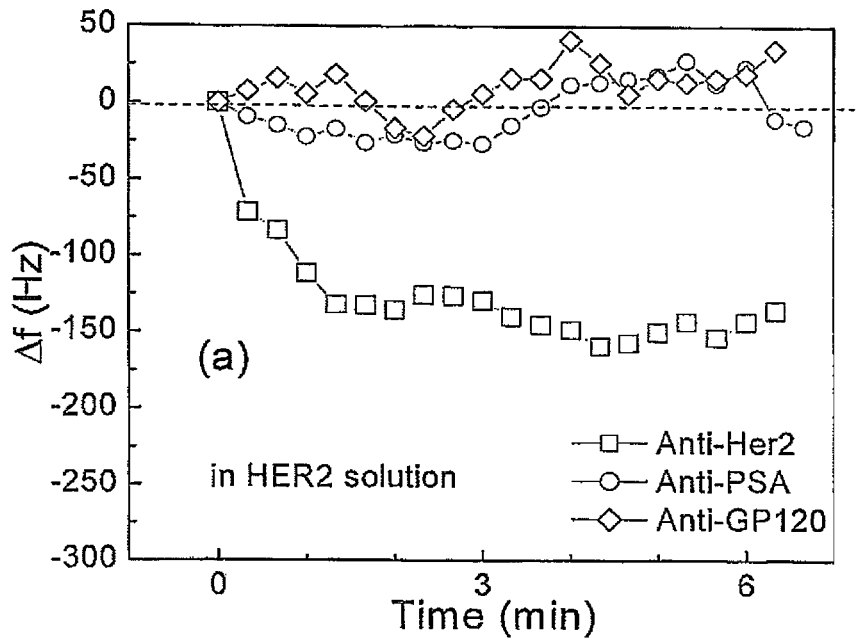
FIG. 13(a) is a graph of resonance frequency shifts of three piezoelectric cantilevers as a function of time in a HER2 solution.
Figure 13B:
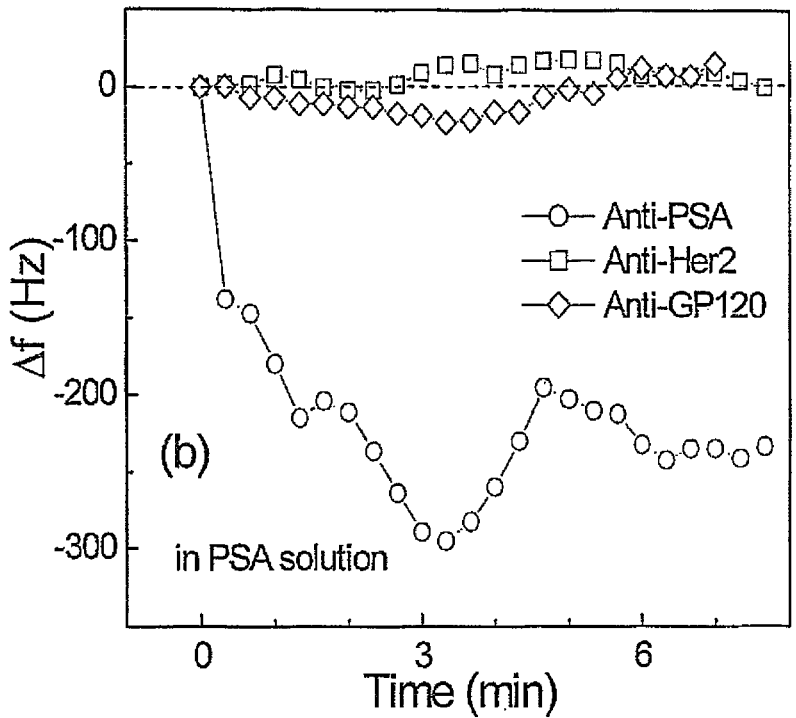
FIG. 13(b) is a graph of resonance frequency shifts of three piezoelectric cantilevers as a function of time in a PSA solution.
Figure 13C:
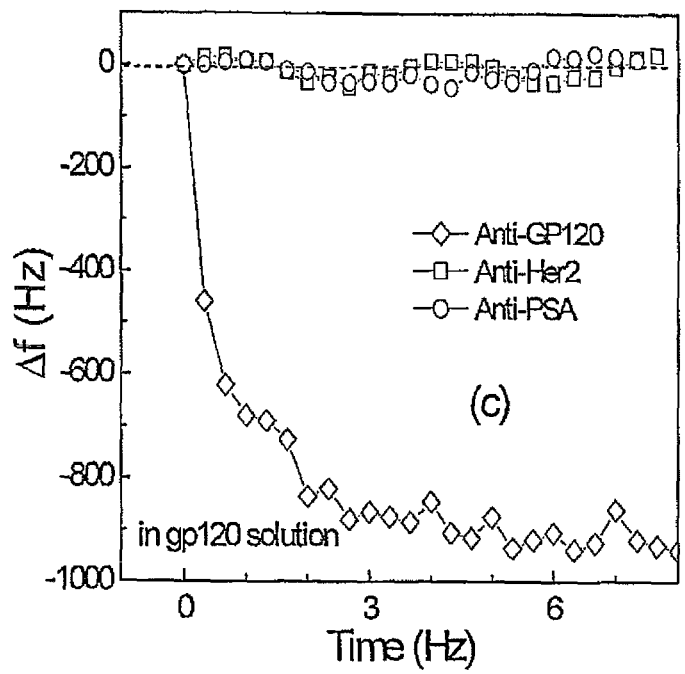
FIG. 13(c) is a graph of resonance frequency shifts of three piezoelectric cantilevers as a function of time in a gp120 solution.

The PEMS of the present invention may also be utilized for simultaneous detection of multiple antigens using a piezoelectric cantilever array. In an experiment, three piezoelectric cantilever sensors were utilized for simultaneous detection of three proteins. One sensor was coated with antibodies specific to PSA, a second sensor was coated with scFv specific to HER2 and a third was coated with antibodies specific to gp120. FIGS. 13(a), 13(b) and 13(c) show the resonance frequency shifts of three PECS over time in various solutions, one coated with scFv of HER2, one coated with an antibody to PSA and one coated with an antibody of gp120. FIG. 13(a) shows the detection results when the PECS are placed in a HER2 solution of 23 ug/ml. FIG. 13(b) shows the detection results when the PECS are placed in a PSA solution of 18 µg/ml, and FIG. 13(c) shows the detection results when the PECS are placed in a gp120 solution of 100 µg/ml. FIG. 13(a) shows that only the PECS coated with scFv of HER2 responded to the HER2 solution. Similarly, only the PECS coated with antibodies to PSA responded to the PSA solution of FIG. 13(b), and only the PECS coated with antibodies to gp120 responded to the gp120 solution.

The experiment demonstrated that only sensors coated with antibodies specific to the antigen solution reacted in each of the three solutions. The experiment proves that a cantilever array can perform in-situ, rapid, simultaneous detection of multiple antigens. A portable device may therefore be used to carry multiple sensors for multiple antigen detection in a solution.

Example 5

A number of methods and electrically insulating materials may be used to insulate the electrodes of a PEMS. Parylene and MTMS, in particular, were separately coated on PZT PEMS and evaluated for dampening impedance.

Figure 14A:
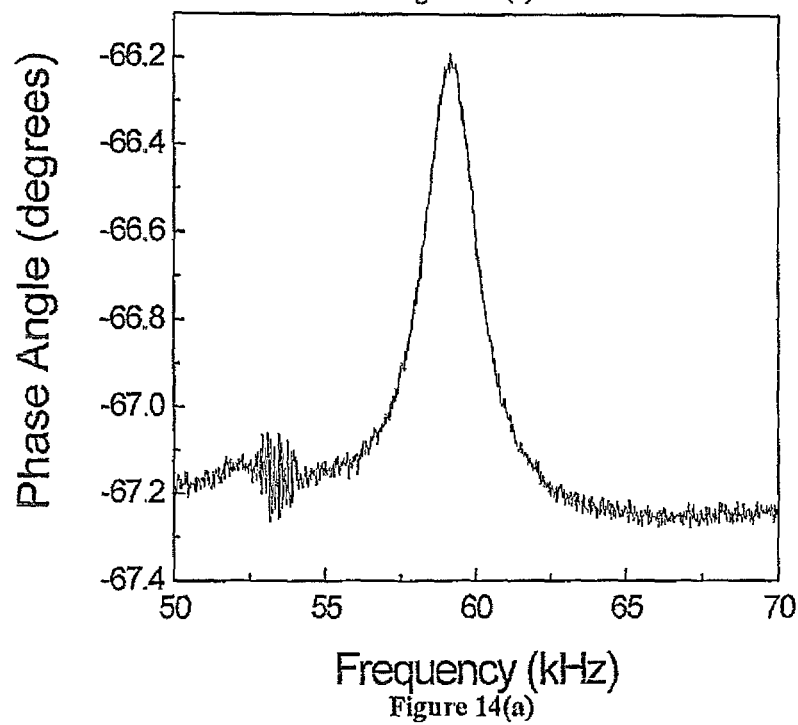
FIG. 14(a) shows the resonance spectra of a parylene insulated PEMS placed in static and 1 ml/min flow solutions of PBS.

FIG. 14(a) shows the impedance resonance spectrum of a parylene insulated PMN—PT/Cu PEMS completely immersed in a static and 1 ml/min flow solution of PBS. The PEMS is insulated with a 1.5 µm thick parylene coating and has a mass detection sensitivity of about $4 \times 10^{-13}$ g/Hz. The background resonance frequency shift was no more than 30 (60) Hz in 30 min in static PBS and in flowing PBS at 1 ml/min. It is expected that at a typical detection flow rate of 0.2-0.5 ml/min, the background resonance frequency shift should be no more than 40 Hz in 30 min. Note that even at 1 ml/min., the resonance peak still retained a Q value well over 35.

Figure 14B:
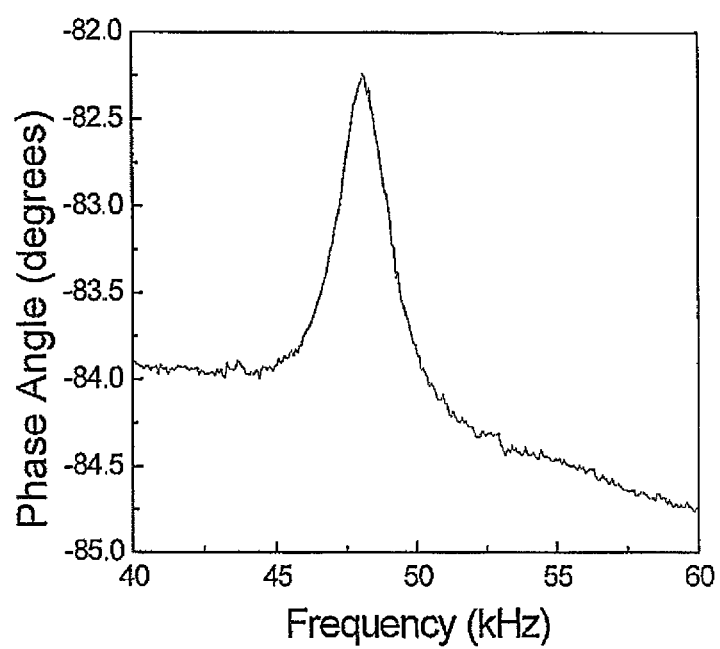
FIG. 14(b) shows graphs of peak shift as a function of time for a parylene insulated PEMS placed in static and 1 ml/min flow solutions of PBS.

FIG. 14 (b) compares the peak position shift with time in static PBS and in a 1 ml/min flow. As can be seen the peak positions were fairly stable with no more than a 30 Hz shift over 30 minutes in static PBS and no more than a 60 Hz shift over 30 minutes at a flow rate of 1 ml/min in PBS. At the typical flow rate 0.2-0.5 ml/min, the background resonance frequency shift is expected to be no more than 40 Hz.

Figure 15A:
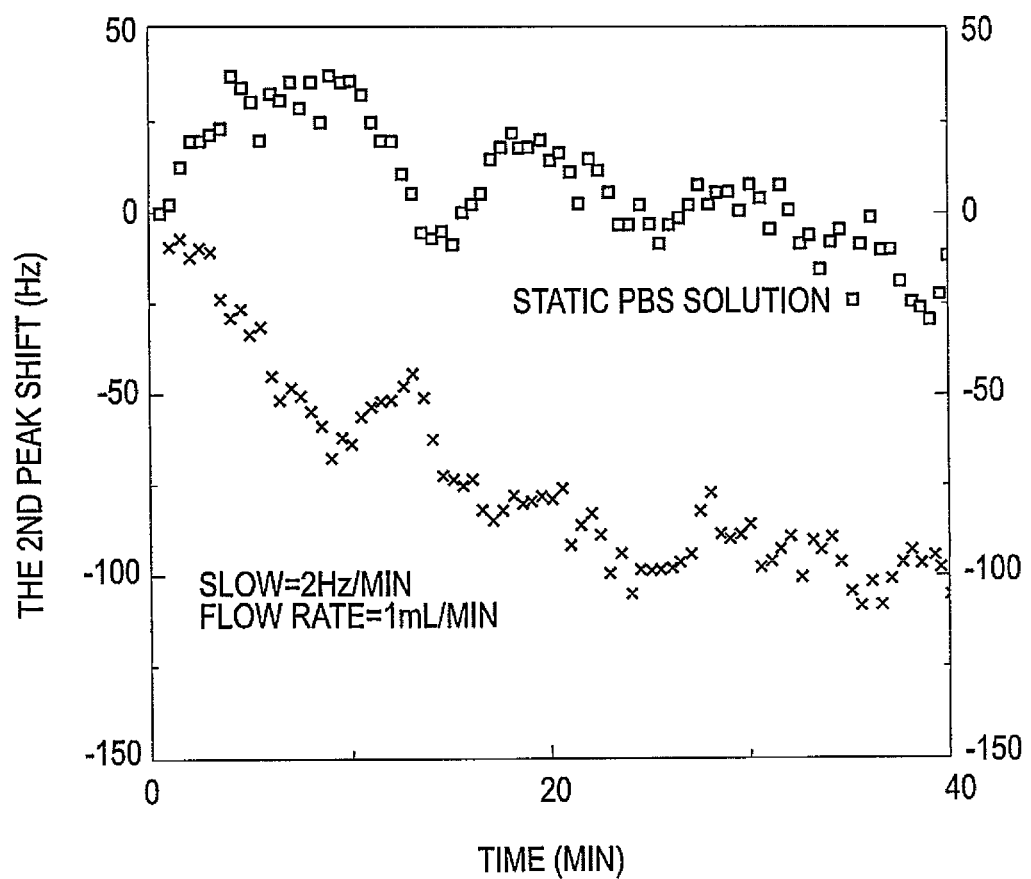
FIGS. 15(a)-15(b) are resonance spectra of a MTMS insulated PZT PEMS placed in a 0.5 ml/min flow solution of PBS.
Figure 15B:
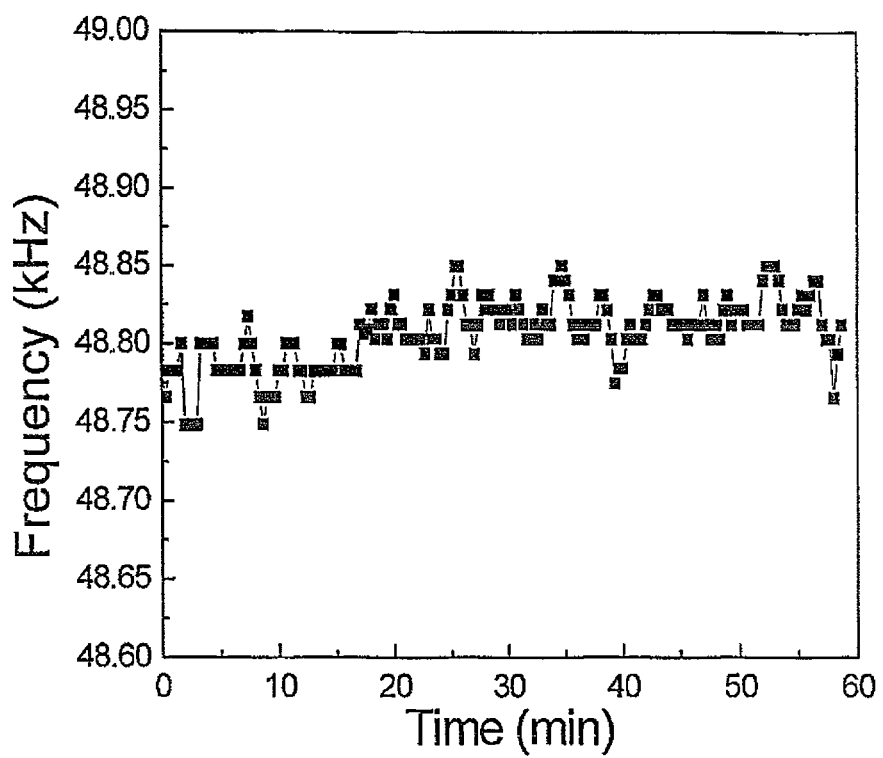

FIG. 15(a) shows the resonance spectrum of a PZT PEMS insulated with a monolayer of MTMS. The PEMS was placed in a flow cell and completely immersed in a 0.5 ml/min flow solution of PBS. It was found to have a mass detection sensitivity of about $5 \times 10^{-11}$ g/Hz. FIG. 15(b) shows the background resonance frequency shift as a function of time in flowing PBS at 0.5 ml/min. The background resonance frequency shift was no more than 30 Hz over 30 minutes. The graphs show that the electrical impedance spectrum was stable with strong resonance peak intensity and indicate that the MTMS monolayer is a good electrical insulation layer.

Example 6

A PMN—PT piezoelectric layer or film may be fabricated using a precursor-suspension method. Submicron crystalline PMN powder was prepared by dispersing $Mg(OH)_2$-coated $Nb_2O_5$ particles in a lead acetate/ethylene glycol solution followed by calcination at about 800° C. The crystalline PMN powder was subsequently suspended in a PT precursor solution containing lead acetate and titanium isopropoxide in ethylene glycol to form a PMN—PT precursor powder, which can be sintered at a temperature as low as about 900° C.

The PMN—PT films were then polarized in order to obtain high piezoelectric coefficients. Before polarization, the orientations of domains were random with no net polarization. After polarization, many domains were aligned in the direction of the applied electric field resulting in a finite polarization. Although polycrystalline materials are not easily aligned in comparison to single crystal materials, PMN—PT films were geometrically structured so as to facilitate polarization alignment within the plane of the film.

The resulting freestanding PMN—PT films were then electroplated on one side with a sputtered 30 nm thick nickel/platinum (Ti/Pt) layer. A copper layer of appropriate thickness was then electroplated on the Pt surface to create a non-piezoelectric layer, followed by the deposition of the Ti/Pt electrode on the other face of the film. A PMN—Pt/Cu bi-layer was then embedded in wax and cut or chemically etched to form a cantilever shape with a wire saw.

A particularly advantageous aspect of this method is the ability to construct a microcantilever from one piece of PMN—PT film without having to separately attach the non-piezoelectric and piezoelectric layers, facilitating the manufacturing process. Because the cantilevers, thus fabricated, had a clean geometry and clean interfaces between the PMN—PT layer and the electrodes, cantilever sensitivity was heightened, as demonstrated by Q values as high as 300.

The resulting suspensions have previously been used to formulate PMN—PT freestanding films of about 8-75 μm thick upon sintering at 1000° C. Typically, the freestanding PMN—PT films have femtogram sensitivity of at least $2 \times 10^{-14}$ g/Hz, dielectric constants greater than 1000, saturated polarization of about 30 μC/cm$^2$, remnant polarization of 25 μC/cm$^2$ and a Q value as high as 300. Therefore PMN—PT microcantilevers are capable of generating higher-mode resonance peaks resulting in enhanced sensitivity detection.

Example 7

A PZT/SiO$_2$ piezoelectric layer of film may be formed on silicon wafers and attached to a substrate, such as glass, to form an array. FIG. 3 depicts a preferred micro-fabrication procedure for constructing PZT/SiO$_2$ piezoelectric microcantilever sensors. A low-stress SiO$_2$ substrate, 2-μm in thickness, was first deposited on front and back sides of a (100)-oriented silicon wafer by steam oxidation at 800° C. A first side of the SiO$_2$ constituted the non-piezoelectric layer of the microcantilever, and a second side of the SiO$_2$ formed an etching mask, wherein the silicon wafer was wet etched using KOH.

A 400 Å thick TiO$_2$ bonding layer was then deposited by reactive sputtering of Ti followed by the deposition of a 1500 Å thick platinum electrode. Reactive sputtering of Ti was carried out under 15 mTorr of 80% oxygen and 20% helium. To prepare for deposition of the platinum electrode, a stage or platform was heated to 650° C. at a rate of 5° C./min. The RF power was adjusted to the expected deposition rate. After deposition, the stage was cooled to room temperature at a rate of 5° C./min to avoid residue stress. Sputtering of the platinum bottom electrode began when the stage reached room temperature. The resultant platinum bottom electrode was preferably about 1500 Å in thickness.

A 1.5-μm thick PZT layer was then deposited on the Pt/TiO$_2$/SiO$_2$/Si substrate using a sol gel method with repeated spin coating and heat treatment steps. According to the sol gel method, titanium isopropoxide and lead acetate were dissolved in ethylene glycol and zirconium-n-propoxide in 2-propanol. The dissolved components were mixed to obtain a PZT precursor solution. The precursor solution also contained a 50% excess of lead to compensate for lead loss during repeated heat treatment. The PZT thin films were then deposited by repeated spin coating on a Pt/TiO$_2$/SiO$_2$ substrate followed by pyrolysis at 350° C. for 12 min and sintering at 650° C. for 2 hours after every 5 depositions. The Pt/TiO$_2$/SiO$_2$ substrate was formed by depositing a 2-μm thick low-stress SiO$_2$ on a silicon wafer through steam oxidation, depositing 40 nm of Ti on the SiO$_2$ by sputtering and oxidization at 800° C. and depositing 150 nm Pt by sputtering to prevent undesired interfacial reaction and diffusion. The TiO$_2$ buffer and a SiO$_2$ layer, having a thickness larger than 0.5 μm, together effectively eliminated diffusion between the PZT layer and the substrate.

After forming the PZT layer, a first electrode, Pt/Ti or Au/Cr, was deposited by E-gun evaporation in high vacuum ($2 \times 10^{-6}$ torr or lower) to avoid oxidation of metal, particularly oxidation of the Cr layer. E-gun evaporation was used because it is gentler than sputtering or thermal evaporation and avoids damaging the PZT layer. The thickness of the resultant Ti or Cr bonding layer was approximately 5-40 nm and the resultant Pt or Au electrode was approximately 100-200 nm thick. A nickel layer was deposited on the top electrode to form a hard mask for protecting the top electrode and the underlying PZT during dry etching. The Ni and top electrode were patterned using an over-hang lift-off process. LOR10B and SPR3012 photoresists are recommended for executing the over-hang lift-off process, and the thickness of the undercut photoresist (LOR) was about 0.8 to 1.2 μm, approximately 1.5 times larger than the metal layer. The selectivity or etching rate ratio of PZT to Ni was nearly 5:1. The thickness of the resultant Ni layer was about 0.3-0.5 μm, depending on the PZT thickness.

The exposed PZT and TiO$_2$/Pt bottom electrode was patterned by a chlorine-based inductively coupled plasma (ICP) dry etching process using a chlorine etching gas to expose the SiO$_2$ and 150 sccm flow rate. The pressure of the etching chamber was set to below 10 mTorr. The RF power was adjusted to the etching rate. Since the PZT is a ceramic material and the nickel etching mask is stable at high temperatures, a high RF power of about 400 W is recommended for PZT dry etching. The selectivity ratios of the PZT dry etching process were 5:1 for Ni and 8:1 for Pt. The etching mask for the bottom electrode was a thick photoresist such as one in the SPR220 series. Because the etching mask was a photoresist, a low RF power was recommended for this etching process. Silver glue was used to fill spaces between the sample and the stage to help dissipate heat during etching. For every 5 min of etching, a 20-min cooling period was required. By keeping the etching temperature below 120° C., the PR was easily removed with acetone after etching.

The silicon dioxide on the second side was patterned by photolithography, and the exposed silicon dioxide was etched by CF$_4$/CHF$_3$ based reactive ion etching (RIE). After the silicon-dioxide etching is finished, the whole first side was sealed by black wax, and the sample was placed in a 45% potassium hydroxide (KOH) solution. The temperature of the solution was set to 55-60° C., and the KOH was used to etch the exposed silicon with the remaining silicon dioxide as an etching mask.

After etching, the black wax was dissolved using trichloroethylene (TCE) and the front side was cleaned. The exposed silicon dioxide was removed on the front side by a CF$_4$/CHF$_3$-based reactive ion etching (RIE). The first electrode and second electrode work together because the mask and the selectivity ratios are very high. If desired, the etching duration may be increased to ensure that all the silicon dioxide is removed and the cantilevers are released. After rinsing with acetone, 2-proponal and deionized water, free-standing PZT/SiO$_2$ piezoelectric microcantilever sensors were obtained.

Example 8

Mercaptopropylsilane (MPTS) was investigated for its ability to function both as an electrical insulator and as receptor immobilizer. The results established that MPTS is an effective insulator and immobilizer enabling the detection of the HER2 antibody both in solution and in the presence of BSA.

To prepare the MPTS coated PEMS, a PMN—PT/tin PEMS was first soaked in a diluted (1:100 in water) piranha solution, containing two parts 98% sulfuric acid and one part of 30% hydrogen peroxide, at 20° C. for 1 min to clean the tin and gold surfaces. Next, the PEMS was submerged in a beaker containing a 40 mM solution of MPTS in ethanol, and the beaker was covered with paraffin film to prevent ethanol evaporation. After 4 hours, the PEMS was rinsed with DI water and submerged in a 0.01 M solution of NaOH overnight for cross-linking. The PEMS was then soaked in DI water for 1 hour and dried overnight in a vacuum-oven at 762 mm Hg to ensure all the water was removed. The PEMS was then submerged in a 1 volume percent solution of MPTS in ethanol titrated to a pH 4.5 with acetic acid. The solution was covered with paraffin film to prevent ethanol evaporation, and the PEMS was allowed to soak for 8 hours. The PEMS was again soaked in DI water for 1 hour and dried overnight in a vacuum-oven at 762 mm Hg.

Figures 16A, 16B:
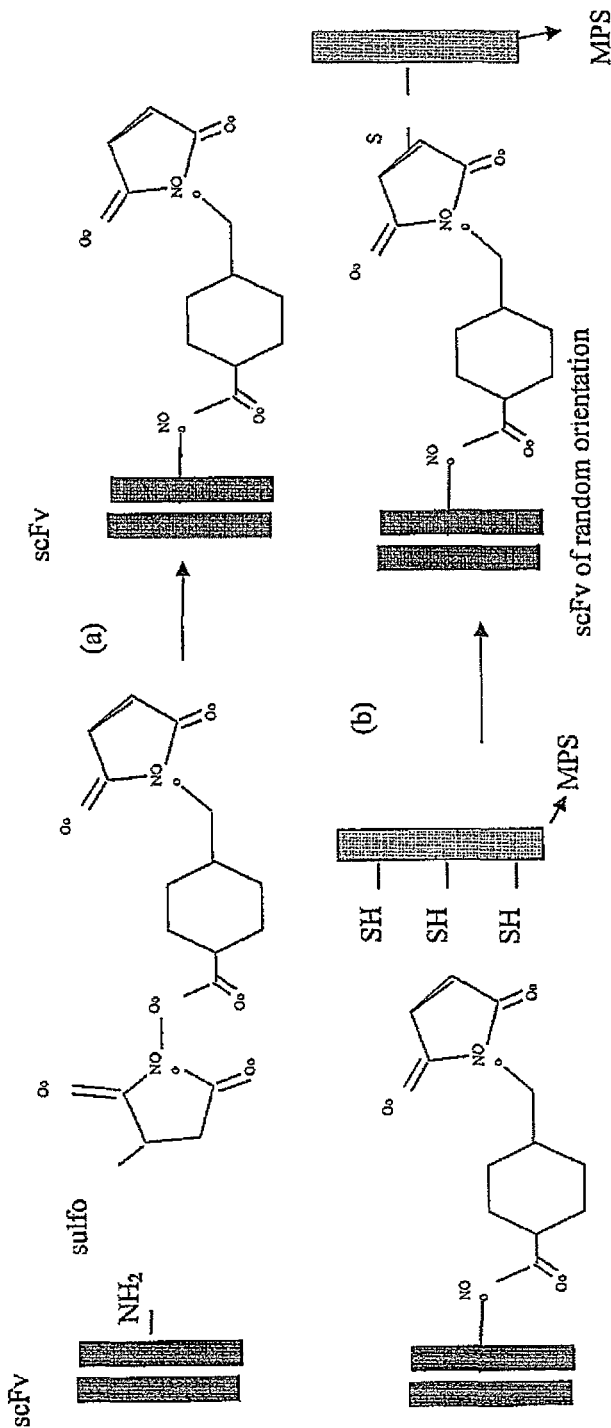
FIG. 16(a) shows a schematic diagram of binding an NHS ester of the SMCC to a primary amine of the scFv.
FIG. 16(b) shows the formation of a thioether bond between the maleimide of the SMCC and the sulfhydryl group of the MPS on the sensor surface.

To immobilize the scFv receptors on the PEMS surface, sulfosuccinimidyl-4-(N-maleimidomethyl)cyclohexane-1-carboxylate (Sulfo-SMCC) was first mixed with scFv to form a peptide bond between a primary amine of the scFv and the NHS ester of the Sulfo-SMCC as depicted in FIG. 16(a). To effectively bind SMCC to scFv, 5 mM SMCC was mixed with 400 nM scFv for 2 hrs. The unreacted SMCC was then removed by repeated microcentrifugation with a 10 kD filter a total of 4 times. The MPTS-coated PEMS was then soaked in the scFv-bound bound SMCC solution.

FIG. 16(b) illustrates the reaction between the sulfhydryl of the MPTS on the sensor surface with the maleimide of the scFv-bound SMCC to immobilize the scFv. The immobilized scFv has random orientation. After immobilization, the PEMS was placed in a mild quenching solution of DI water for 1 hr to quench the unreacted NHS functionalities on the SMCC. Since any primary amine of the scFv could react with the NHS ester of the SMCC the resultant immobilized scFv would be randomly oriented as schematically shown in FIG. 16(b). With the cysteine tag engineered at the base of the scFv, it is now possible to covalently bind the scFv to the sensor surface and at the same time orient the scFv for optical antigen-scFv binding.

For HER2 detection, the scFv-immobilized PMN—PT/tin PEMS was immersed in a home-built flow cell with a peristaltic pump. First PBS was allowed to flow across the conjugated surface for 10 minutes in order to obtain a background reading. Next, a blocking solution of 10 mg/ml of BSA in PBS was allowed to flow over the surface of the cantilever until no significant deviations are observed in the cantilevers resonant frequency. The cantilever was then gently rinsed with a solution of TWEEN-20 followed by PBS. PBS was then allowed to flow across the surface of the cantilever for 10 minutes to ensure that there was no background drift. The flow cell contained 3 ml of HER2 solution. The detection was carried out with two faces of the PEMS tangential to the flow at a flow rate of 0.5 ml/min. After each detection, the HER2 was released from the PEMS surface by flushing with a glycine/HCl solution having a pH of about 2.5 or a supersaturated solution of NaCl. Following the release, the PEMS was then exposed to a suspension of a different concentration for another detection run.

Figure 17A:
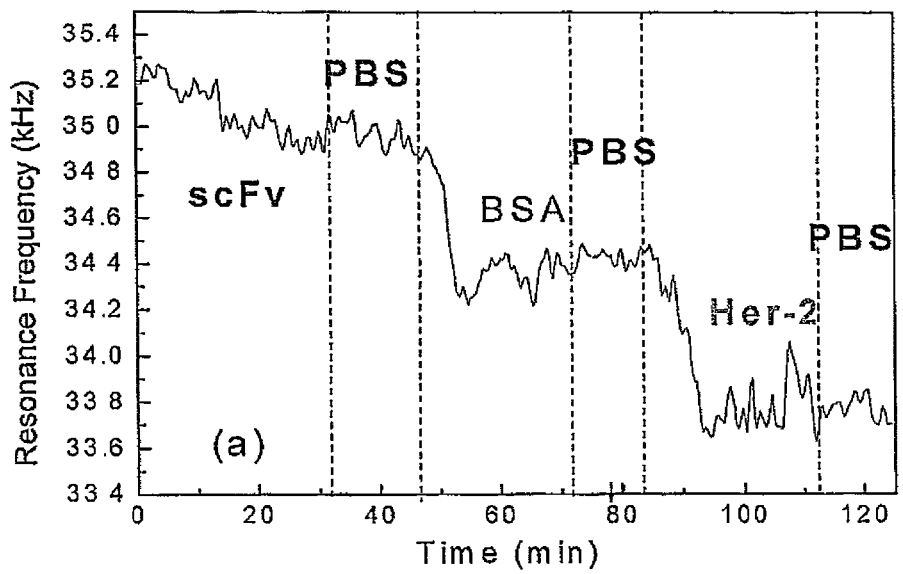
FIG. 17(a) shows a graph of resonance frequency as a function of time during scFv immobilization, PBS rinsing, blocking in a 10 mg/ml of BSA solution, and detection in a 100 ng/ml pure HER2 solution for a PMN—PT/Sn PEMS insulated by MPS.
Figure 17B:
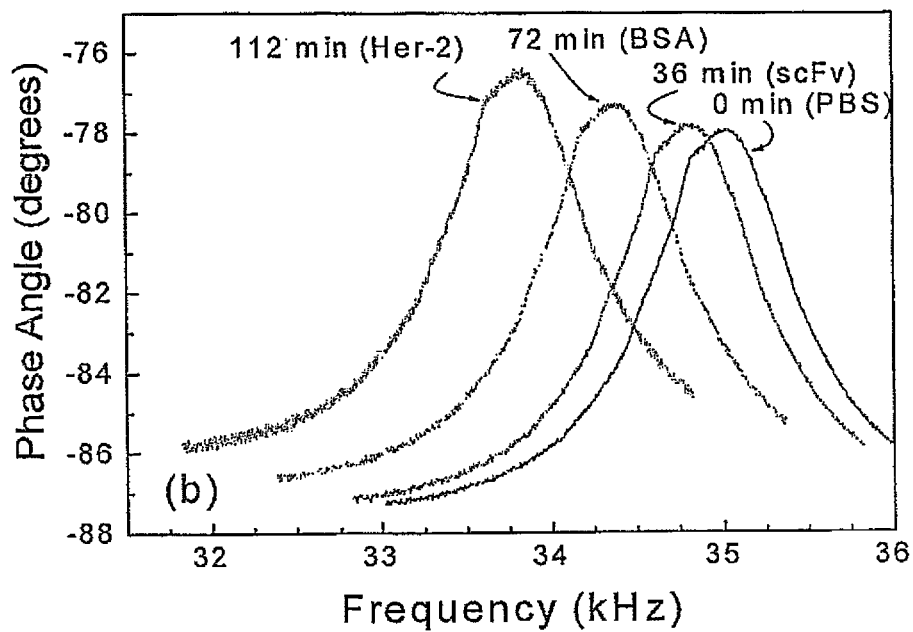
FIG. 17(b) shows resonance spectra at various time frames of FIG. 17(a).
Figure 17C:
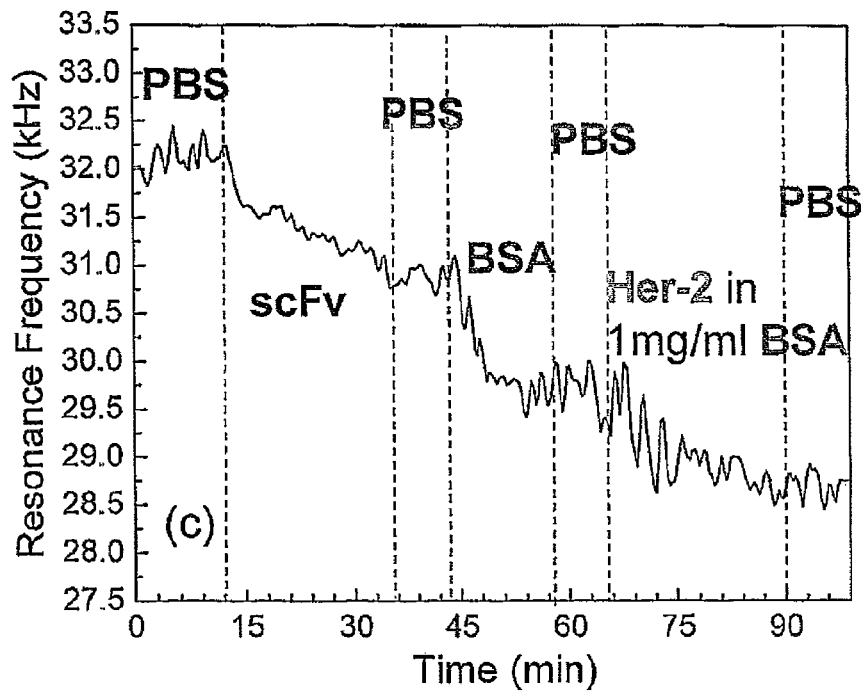
FIG. 17(c) shows a graph of resonance frequency as a function of time during scFv immobilization, PBS rinsing, blocking in a 10 mg/ml of BSA solution, and detection in a 100 ng/ml of HER2 solution and 1 mg/ml BSA solution for a PMN—PT/Sn PEMS insulated by MPS.
Figure 18:
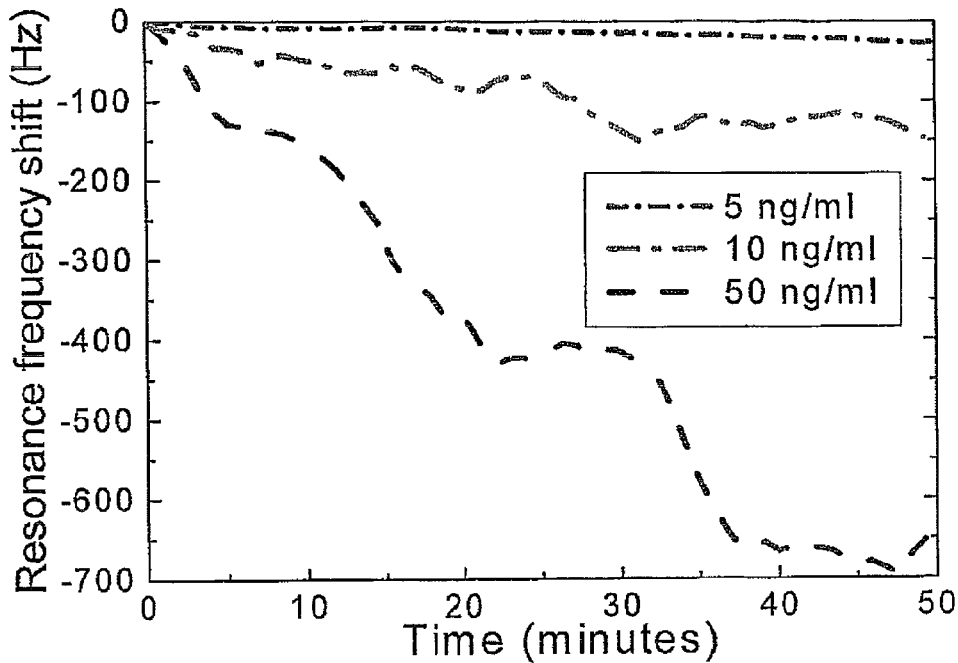
FIG. 18 is a graph of resonance frequency shift as a function of time of a PMN—PT/Sn PEMS insulated with MPS with scFv immobilized via SMCC coupling at 5, 10, and 50 ng/ml of HER2. The insert is a blow-up that shows the resonance frequency shift at 5 and 1 ng/ml HER2.

FIGS. 17(a)-17(c) show the in-situ results of scFv immobilization, the subsequent BSA blocking and detection of 100 ng/ml of HER2 alone, and in the background environment of BSA, using the MPTS-insulated PMN—PT/Sn PEMS. FIG. 17(b) shows that the MPTS-coating was effective as an electrical insulation layer as the resonance peak maintained the same high Q value throughout the 2 hour detection period. In addition, FIGS. 17(a) and 17(c) illustrate that HER2 can be detected in the background environment of BSA. After BSA blocking, the resonance frequency shift for detecting HER2 alone, FIG. 17(a), and in the presence of BSA, (FIG. 17(c), was roughly the same, indicating that the BSA blocking procedure effectively saturated the nonspecific binding sites of BSA and had no observable effect to the PEMS resonance frequency shift. FIG. 18 shows the resonance frequency shift versus time in HER2 detection at 5, 10, and 50 ng/ml in a background of 1 mg/ml BSA using the MPTS-insulated PMN—PT/Sn PEMS. As can be seen, the detection yielded −50 Hz, −150 Hz, and −700 Hz after 50 min at 5, 10, and 50 ng/ml, respectively, indicating that the present PMN—PT/Sn PEMS is capable of detecting HER2 in a background of BSA whose concentration was one million fold higher than that of HER2.

Example 9

The PEMS is capable of in situ detection applications. A one-sided PEMS was able to detect the presence of HER2 in the presence of Bovine Serum Albumin (BSA).

The tin surface of a PMN—PT/Sn PEMS was insulated using MTMS. The scFv receptors were immobilized only on the platinum side of the electrode by first coating the platinum surface with an activated MPA self assembly monolayer to bind to a primary amine of the scFv.

Figure 19:
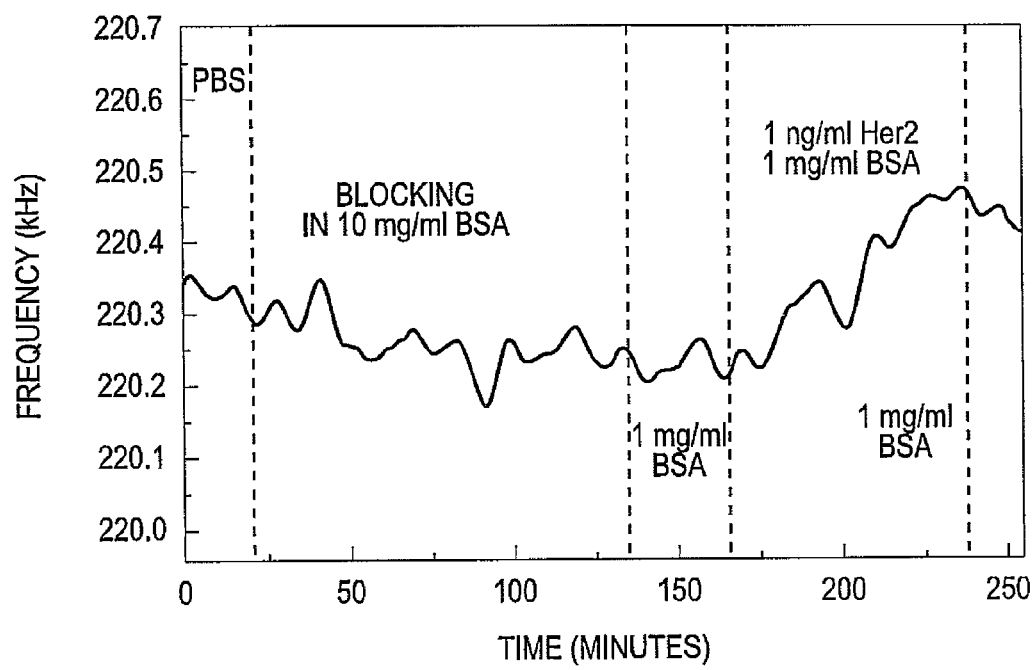
FIG. 19 is a graph of resonance frequency as a function of time of a one-sided PMN—PT/tin PEMS during the various stages of detection of HER2 at 1 ng/ml in a background of 1 mg/ml BSA.

A one sided PMN—PT/tin PEMS was found capable of detecting of HER2 at a concentration of 1 ng/ml in the presence of 1 mg/ml of BSA in a 30 ml solution flowing at a rate of 1 ml/min. FIG. 19 shows a resonance increase in the presence of HER2, indicating that the PEMS was capable of detecting 1 ng/ml of HER2 in 1 mg/ml of BSA.

The BSA did not adhere to the MPA surface to the same degree as compared to the MPTS—SMCC surface of FIGS. 17(a) and 17(c). In the presence of 1 mg/ml BSA, the resonance frequency of the PMN—PT/tin PEMS was stable as shown at t=150 of FIG. 19. In comparison, in the presence of 1 ng/ml of HER2 and 1 mg/ml of BSA, the resonance frequency of the PEMS increased by about 200 Hz during a 160<t<240 interval. Upon the removal of the HER2, the resonance frequency stabilized, suggesting that the one-sided PMN—PT/tin was able to detect the presence of HER2 at 1 ng/ml in the presence of 1 mg/ml of BSA. Note that resonance frequency increase upon binding of target antigens on the sensor surface is common with one-sided detection due to the stress imbalance from the one-sided binding.

FIGS. 17-19 clearly demonstrate that PMN—PT/tin PEMS were able to detect HER2 in situ at a concentration as low as 1 ng/ml in the presence of a 1 mg/ml BSA background, which is lower than the normal 15 ng/ml HER2 concentration of a typical healthy woman. Therefore, these results suggest that PEMS would be able to detect breast cancer markers in serum with useful levels of sensitivity and specificity.

Example 10

A 900 μm long and 500 μm wide PMN—PT/Cu PEMS having an 8 μm thick PMN—PT layer and a 3 μm thick copper layer was used to detect the presence of HER2 in diluted fetal bovine serum (FBS).

The PEMS was prepared using mercaptopropyltrimethoxysilane (MPS) as an insulation layer and covalent receptor conjugation. Biotin was covalently bound to the sulfhydryl of the MPS using maleimide-$PEO_2$-biotin (Pierce). Avidin was subsequently attached to the biotin by soaking the surface of the cantilever in a 1 mg/ml solution of neutravidin (Pierce). Sulfosuccinimidyl-6-[biotinamido]-6-hexanamido hexanoate (Pierce) was used to attach biotin to the primary amine in a scFv. The avidin coated PEMS was then submerged in the solution containing the biotinylated scFv for 60 minutes at 4° C. The cantilever was subsequently soaked in a 3% BSA solution for 2 hours to facilitate blocking of unreacted areas. The PEMS was then rinsed with a 1% BSA solution and a 1% Tween® 20 solution.

Figure 20:
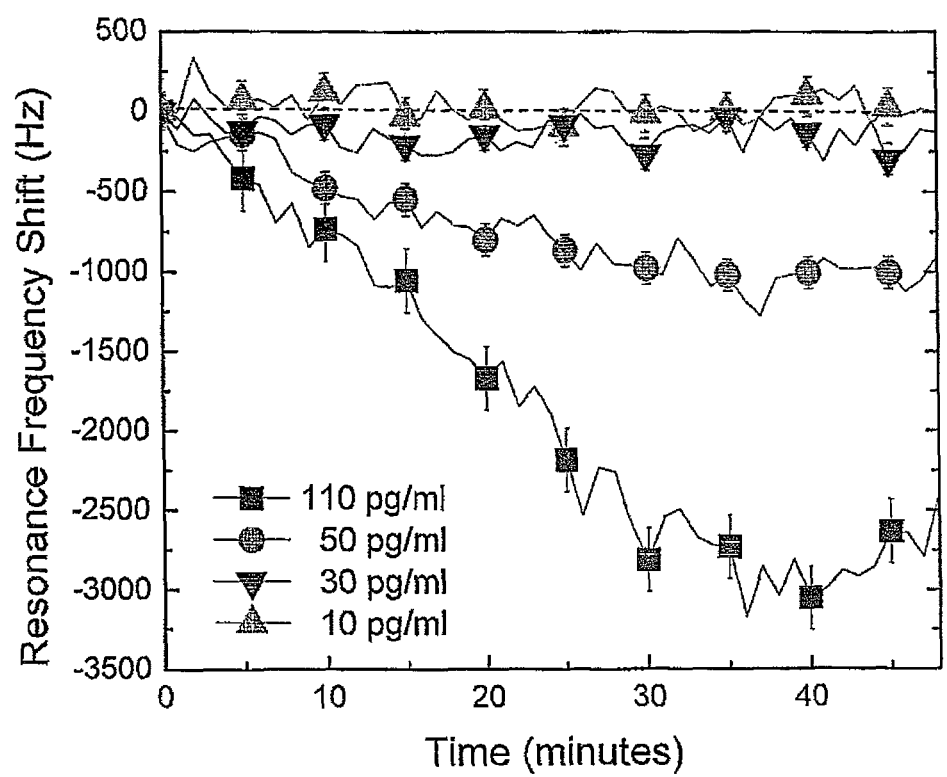
FIG. 20 is a graph of resonance frequency as a function of time showing the detection of HER2 in solutions containing diluted 1:40 fetal bovine serum and HER2 in a concentration of about 110 pg/ml, 50 pg/ml, 30 pg/ml or 10 pg/ml using a PMN—PT/Cu PEMS.

For HER2 detection, the scFv-immobilized PEMS was then immersed in a flow cell containing about 6 ml of liquid with a peristaltic pump. After conjugation, the PEMS was exposed to a solution containing diluted 1:40 bovine serum and HER2 in one of the following concentrations: about 110 pg/ml, 50 pg/ml, 30 pg/ml, and 10 pg/ml. FIG. 20 shows the resonance frequency shift versus time for the PEMS. As can be seen, the PEMS yielded a resonance frequency shift of about 2800±200, 1000±100, 140±100, and 10±100 Hz at t=50 minutes, for 110, 50, 30 and 10 ng/ml HER2 concentrations, respectively. The results indicate the PEMS was able to detect breast cancer markers in diluted serum with a concentration limit of 30 pg/ml.

Example 11

An array of three millimeter long PZT/glass PEMS were used to assess the binding ability of a receptor for its ligand. The performance of 3 receptors, B1 scFv, H3 scFv, and Herceptin, was compared using an array of three identical PZT/glass PEMS insulated with MPS. A heterobifunctional cross linking agent, sulfosuccinimidyl 4-N-maleimidomethyl cyclohexane-1-carboxylate, was used to covalently attach the receptor to the MPS surface. After receptor immobilization the cantilevers were blocked using a 3% BSA solution for 1 hour, and then rinsed with a 1% BSA solution and a 1% Tween® 20 solution.

Figure 21A:
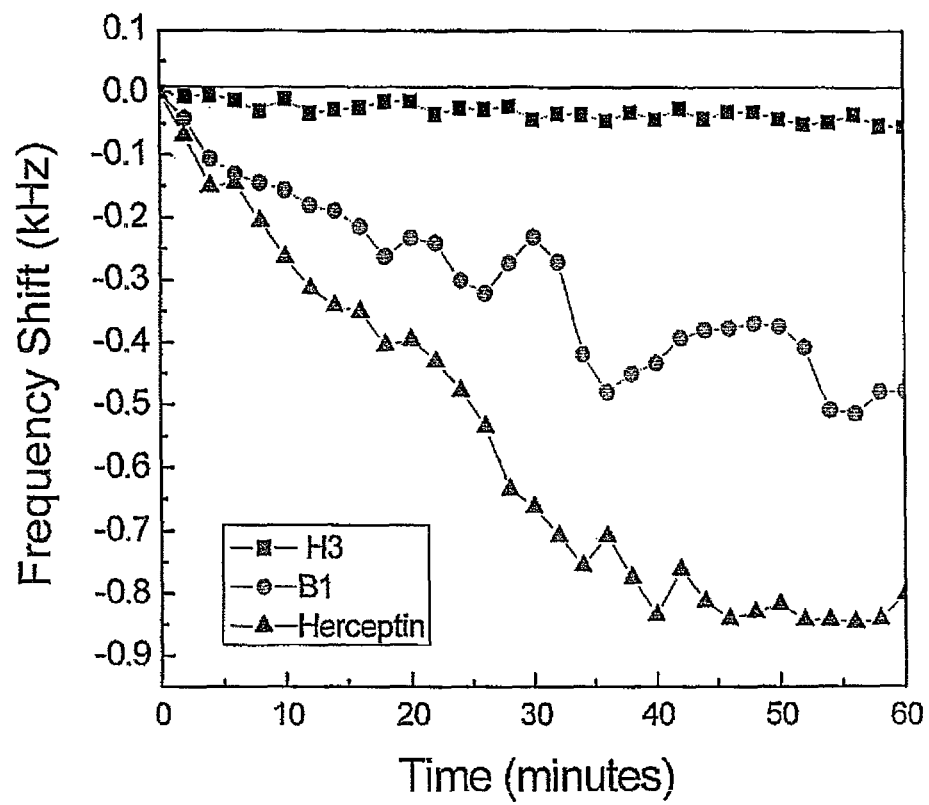
FIG. 21(a) is a graph of resonance frequency shift as a function of time showing the detection of HER2 in a solution of diluted (1:40) fetal bovine serum containing a 6 ng/ml concentration of HER2 using three different receptors.
Figure 21B:
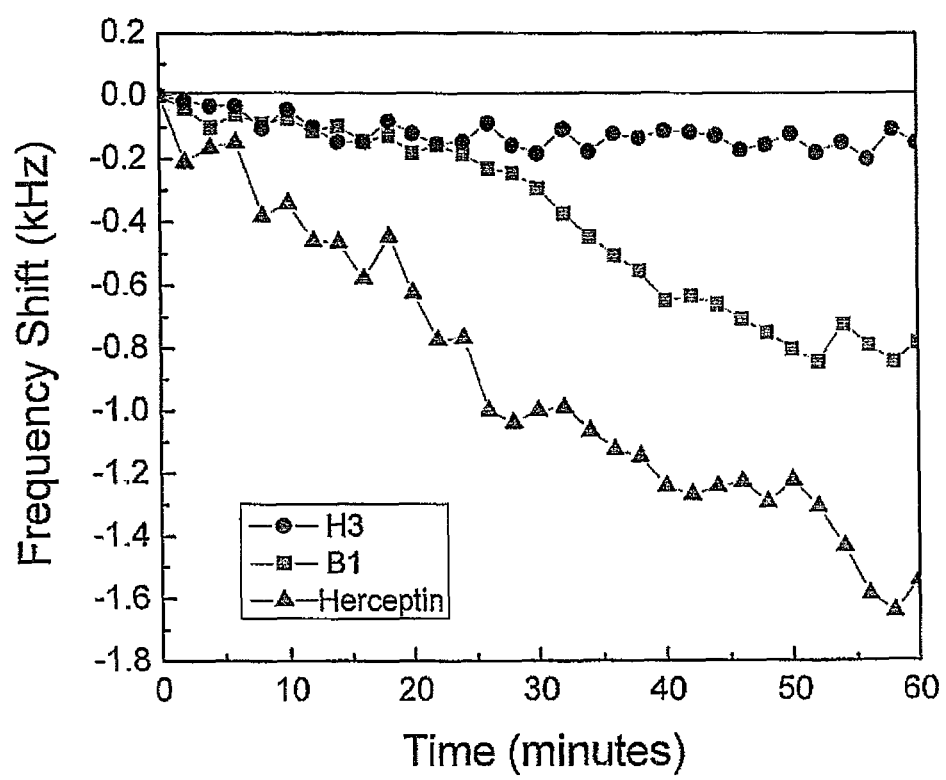
FIG. 21(b) is a graph of resonance frequency shift as a function of time showing the detection of HER2 in a solution of diluted (1:40) fetal bovine serum containing a 60 ng/ml concentration of HER2 using three different receptors.
Figure 21C:
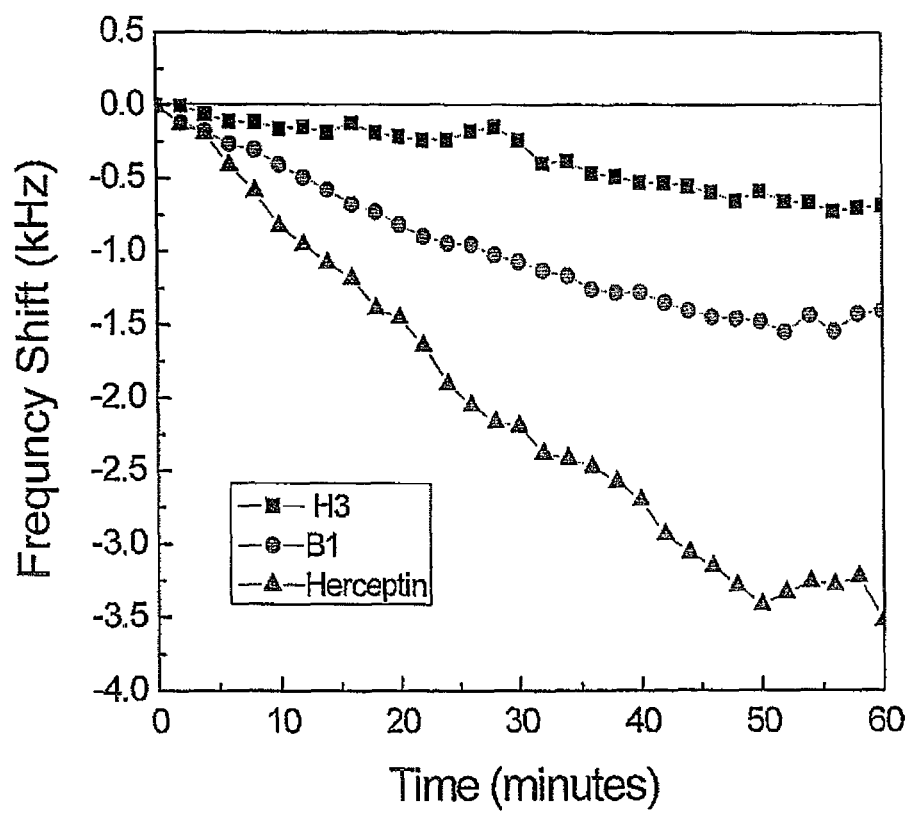
FIG. 21(c) is a graph of resonance frequency shift as a function of time showing the detection of HER2 in a solution of diluted (1:40) fetal bovine serum containing a 600 ng/ml concentration of HER2 using three different receptors.

The three PEMS were all completely submerged in the same 6 ml flow cell. A 1:40 fetal bovine serum diluted in PBS containing a known spiked amount of HER2 ECD was introduced into the flow cell. The sample was flowed through the system at a rate of 0.7 ml/minute. FIG. 21 shows the resultant PEMS detection of HER2 in solutions containing diluted 1:40 fetal bovine serum and HER2 in concentrations of 6 ng/ml, 60 ng/ml or 600 ng/ml. In Table 3, the resonance frequency shift is given at t=60 minutes. According to FIG. 21 and Table 3, the three identical PEMS showed that Herceptin consistently had larger frequency shifts, suggesting that Herceptin can be detected using PEMS at a lower concentration limit, as compared to B1 scFv and H3 scFv.

TABLE 3

Resonance frequency shift of the array PZT/glass PEMS immobilized with different HER2 receptor: H3, B1 and Herceptin.

| Concentration | H3 | B1 | Herceptin |
|---|---|---|---|
| 6 ng/ml | 55 | 460 | 850 |
| 60 ng/ml | 150 | 840 | 1500 |
| 600 ng/ml | 780 | 1300 | 3200 |

Example 12

Figure 22A:
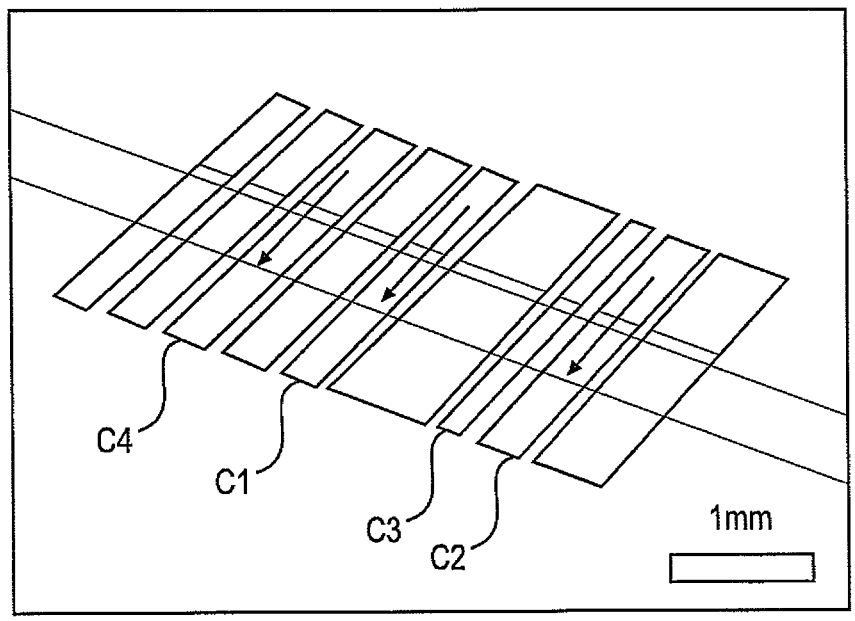
FIG. 22(a) is an optical micrograph of the PZT/glass PEMS array used in the CP detection and FIG. 22(b) is a graph of resonance frequency shift as a function of time showing the detection of CP at a concentration of about 1 CP/ml using 4 different PEMS.
Figure 22B:
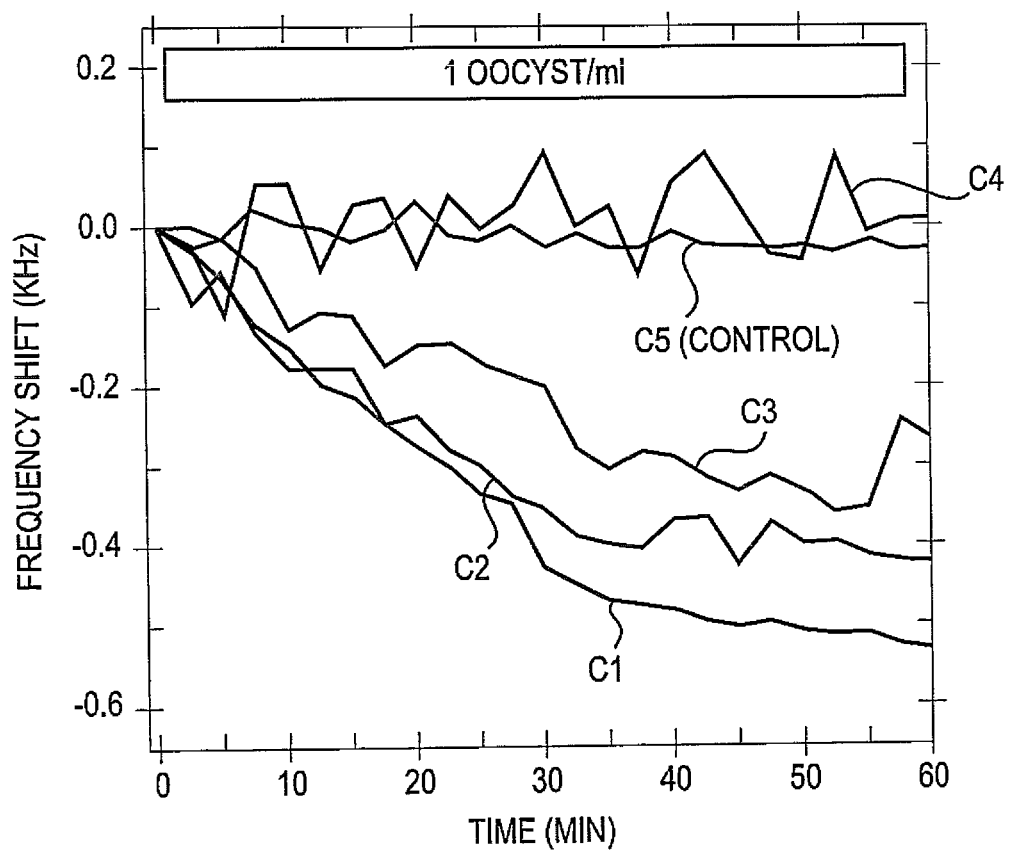

An array of millimeter long PZT/glass PEMS, each having a width of about 300-600 μm and including a 1 mm long PZT layer and a 2 mm long glass tip, as shown in FIG. 22(*a*), was used to detect the water borne parasite, *cryptosporidium parvum* (CP) at concentration levels of 0.1 CP/ml in a volume of 60 ml, i.e., 6 total CPs in the 60 ml of water. The PEMS were insulated with MPS and conjugated with the anti-CP IgM using the bi-functional linker SMCC.

In the experiment, two arrays were used; one control array, whose PEMS were coated with an irrelevant protein BSA (not shown), served as control and one experimental array, whose PEMS were coated with anti-CP IgM. A CP sample was introduced to the PEMS array at a flow rate of about 1 ml/min. FIG. 22(*b*) shows the resonance frequency shift as a function of time for each of the four experimental PEMS coated with anti-CP IgM, i.e. C1, C2, C3, and C4. As can be seen, the control array showed no resonance frequency shift while C1, C2, and C3 showed several hundred Hz resonance frequency shifts, indicating that a PEMS array may be used for CP detection at very low concentrations based on the positive response from any of the PEMS, which indicates the presence of a target pathogen.

Example 13

Figures 23A, 23B:
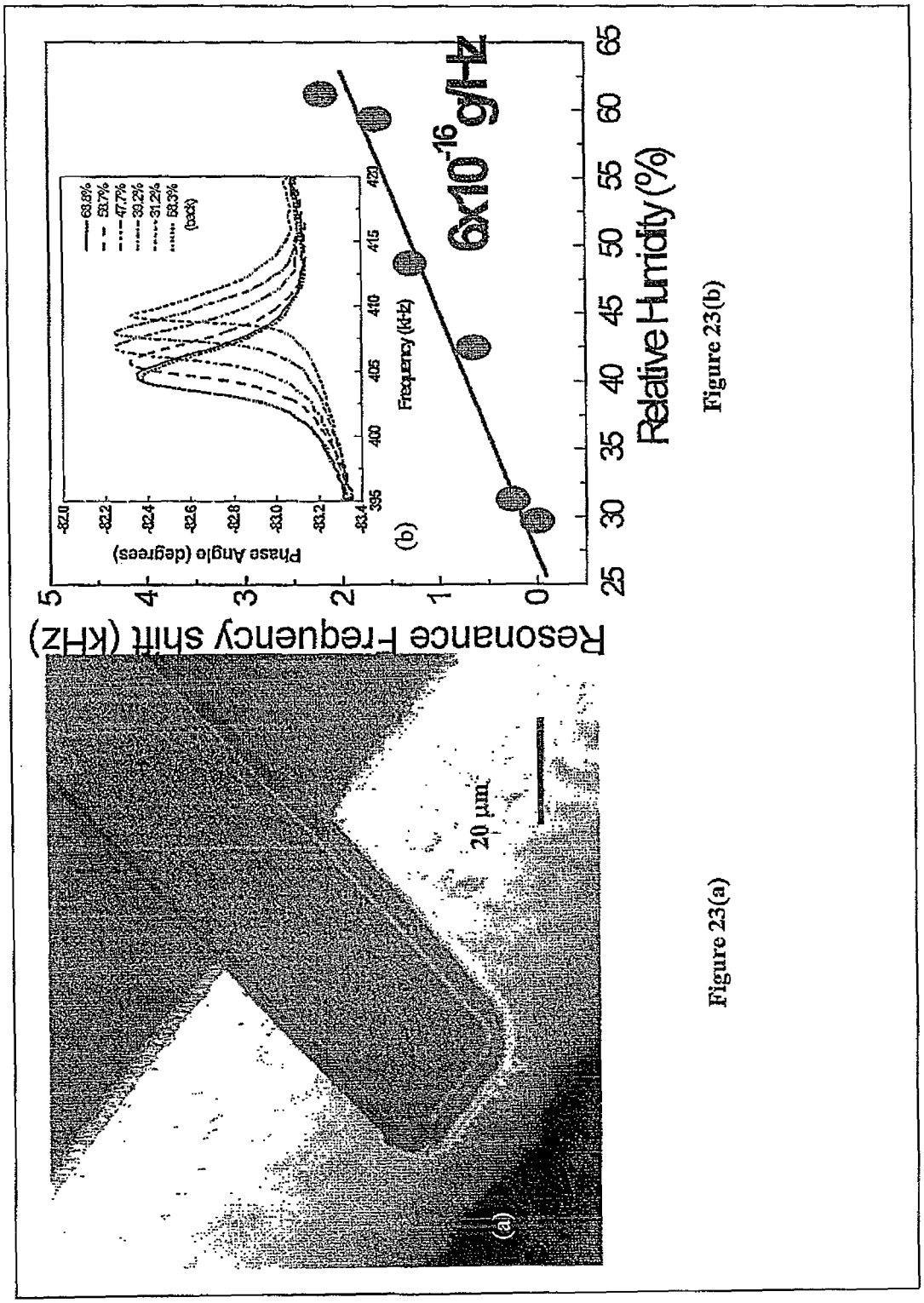
FIG. 23(a) is an SEM micrograph a 40 μm long PZT/SiO$_2$ PEMS.
FIG. 23(b) is a graph of resonance frequency shift versus relative humidity of a 40 μm long PZT/SiO$_2$ PEMS.

A 40 μm long PZT/SiO$_2$ PEMS, as shown in FIG. 23(*a*), was found to have an improved sensitivity of about $10^{-16}$ g/Hz with resonance peak Q values as high as 300 in a humidity controlled environment. FIG. 23(*b*) shows the resonance frequency spectra of the PEMS corresponding to varying humidity. The resonance frequency was found to decrease with an increasing relative humidity due to the adsorption of water molecules on the sensor surface. Therefore it is possible to increase sensitivity with very small PEMS.

The resultant sensitivity of $6 \times 10^{-16}$ g/Hz demonstrates the feasibility of further reducing PEMS size while increasing sensitivity when compared to the millimeter sized commercial PZT PEMS having a sensitivity of about $10^{-11}$ g/Hz and 300-800 μm long PMN—PT PEMS having a sensitivity of about $10^{-13}$ to $10^{-14}$ g/Hz.

Having described the preferred embodiments of the invention which are intended to be illustrative and not limiting, it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, the intended scope of protection is set forth in the appended claims.

The invention claimed is:

1. A method for using a piezoelectric microcantilever sensor comprising the steps of:
    actuating a microcantilever sensor having a Q value greater than 20, comprising a piezoelectric layer, a non-piezoelectric layer, and a receptor, wherein said piezoelectric layer has a thickness of about 1 μm to about 127 μm, a dielectric constant of at least 1600, and a piezoelectric coefficient $-d_{31}$ of at least about 250 pm/V;
    binding a molecule or compound to said receptor,
    detecting a force exerted on said piezoelectric layer by said bound molecule or compound, and
    determining one or more of a presence of said molecule or compound and a concentration of said molecule or compound from said detected force.

2. The method of claim 1, wherein said receptor is selected from the group consisting of DNA, proteins, enzymes, cells, viruses, parasites, antigens and pathogens.

3. The method of claim 1, wherein said molecule or compound is selected from the group consisting of bioterrorism agents, cancer agents, bacterial disease agents and viral disease agents.

4. The method of claim 1, further comprising the step of detecting a resonance frequency shift.

5. The method of claim 1, wherein the microcantilever sensor further comprises an electrical insulation layer which insulates conducting elements of said sensor.

6. The method of claim 5, wherein the electrical insulation layer comprises a material selected from the group consisting of poly-para-xylylene, methyltrimethoxysilane, 3-mercaptopropyl trimethoxysilane, Al$_2$O$_3$, SiO$_2$ and functionalized hydrophobic silanes and mixtures thereof.

7. The method of claim 1, wherein the receptor is bound to a conducting element by an immobilization layer.

8. The method of claim 1, wherein a length of said piezoelectric layer is less than or greater than a length of said non-piezoelectric layer.

9. The method of claim 1, wherein said piezoelectric layer if fabricated from a freestanding film.

10. The method of claim 1, wherein said piezoelectric layer has a thickness of less than 2 μm.

11. The method of claim 1, wherein said piezoelectric layer has a dielectric constant of at least 1900 and a thickness less than 4 μm.

12. The method of claim 1, wherein said piezoelectric layer has a dielectric constant of at least 1900 and a thickness less than 2 μm.

13. The method of claim 1, wherein said piezoelectric layer has a thickness less than 8 μm.

14. The method of claim 1, wherein said piezoelectric layer comprises a material selected from the group consisting of lead magnesium niobate-lead titanate, lead-zirconate-titanate, and doped sodium potassium niobate-lithium niobate.

15. The method of claim 1, wherein said piezoelectric layer comprises a lead-free piezoelectric material.

16. The method of claim 1, wherein said piezoelectric microcantilever has a Q value greater than 120.

17. The method of claim 1, wherein the non-piezoelectric layer comprises a material selected from the group consisting of a ceramic material, a polymeric material, a metallic material and a combinations thereof.

18. The method of claim 1, wherein said non-piezoelectric layer comprises a material selected from the group consisting of silicon dioxide, silicon nitride, tin and copper.

19. The method of claim 1, wherein said non-piezoelectric layer comprises multiple layers of different materials.

20. The method of claim 1, wherein the step of actuating comprises applying a voltage across said piezoelectric layer.

* * * * *